United States Patent [19]

Schumacher et al.

[11] Patent Number: 5,696,258
[45] Date of Patent: Dec. 9, 1997

[54] PROCESS FOR THE PREPARATION OF TRIPHENDIOXAZINE DYESTUFFS AMIDATED ON BOTH SIDES

[75] Inventors: Christian Schumacher, Kelkheim; Karl-Josef Herd, Odenthal, both of Germany

[73] Assignee: DyStar Textilfarben GmbH, Germany

[21] Appl. No.: 744,422

[22] Filed: Nov. 8, 1996

[30] Foreign Application Priority Data

Nov. 10, 1995 [DE] Germany .................. 195 41 985.5

[51] Int. Cl.[6] .................................................. C07D 498/04
[52] U.S. Cl. .................................................. 544/76; 544/77
[58] Field of Search .................................. 544/76, 77

[56] References Cited

U.S. PATENT DOCUMENTS

| | | |
|---|---|---|
| 3,883,523 | 5/1975 | Parton ............................. 260/246 R |
| 4,933,446 | 6/1990 | Sawamoto et al. ................... 544/76 |
| 5,272,267 | 12/1993 | Miyamoto et al. .................. 544/76 |
| 5,405,947 | 4/1995 | Hoppe et al. ..................... 534/618 |
| 5,438,137 | 8/1995 | Miyamoto et al. .................. 544/76 |
| 5,456,726 | 10/1995 | Kawabata et al. ................... 8/549 |
| 5,484,458 | 1/1996 | Russ et al. ........................ 8/549 |
| 5,486,607 | 1/1996 | Miyamoto et al. .................. 544/76 |

FOREIGN PATENT DOCUMENTS

| | | |
|---|---|---|
| 0275022 | 6/1992 | European Pat. Off. . |
| 0325246 | 7/1992 | European Pat. Off. . |
| 0568860 | 11/1993 | European Pat. Off. . |
| 0603823 | 6/1994 | European Pat. Off. . |
| 0385120 | 4/1995 | European Pat. Off. . |
| 2124080 | 6/1975 | Germany . |
| 4316539 | 11/1994 | Germany . |
| 2-238063 | 9/1990 | Japan . |
| 9421646 | 9/1994 | WIPO . |

OTHER PUBLICATIONS

Nishi et al Bulletin of the Chemical Society of Japan, Bd. 56, Nr. 5, May 1983, Tokyo Japan, pp. 1482–1486 XP002026132.

Primary Examiner—Philip I. Datlow
Attorney, Agent, or Firm—Connolly & Hutz

[57] ABSTRACT

According to the invention, a process for the preparation of triphendioxazines symmetrically or asymmetrically amidated on both sides comprises reducing a triphendioxazine chromophore, which is optionally already amidated on one side, to give the leuco form and amidating and re-oxidizing the leuco form. Products amidated on both sides are obtained in this manner with a high yield and product quality. Novel triphendioxazine dyestuffs are furthermore prepared in this manner.

7 Claims, No Drawings

PROCESS FOR THE PREPARATION OF TRIPHENDIOXAZINE DYESTUFFS AMIDATED ON BOTH SIDES

The present invention lies in the field of triphendioxazine textile dyestuffs.

Triphendioxazines are tinctorially strong dyestuffs which are suitable both as direct dyestuffs and as reactive dyestuffs. However, the corresponding dyestuff hydrolysates are often difficult to wash out, and the levelness of the dyeings is unsatisfactory.

Dioxazines amidated on both sides have already been described frequently in the technical literature (for example U.S. Pat. No. 4,933,446, U.S. Pat. No. 5,486,607 and U.S. Pat. No. 3,883,523). However, the compounds amidated on one side are frequently chiefly formed in the procedures described, often in contrast to the statements made, or the products described as being amidated on both sides are formed only in unsatisfactory yields. Thus, the compounds amidated on one side are royal blue, while the compounds amidated on both sides are violet or very reddish-tinged blue. It is furthermore known that an increasingly redder product is formed with excess amidating agents (U.S. Pat. No. 3,883,523), from which partial double amidation can be concluded, although this is achieved selectively in the rarest of cases.

Moreover, customary methods to date for preparation of such triphendioxazine dyestuffs, for example U.S. Pat. No. 5,486,607, U.S. Pat. No. 5,272,267, U.S. Pat. No. 5,438,137 and U.S. Pat. No. 4,933,446, give yields and product qualities which are in need of improvement.

"Amidated triphendioxazine compounds" in the present Application means those compounds in which the exocyclic nitrogen atoms of the triphendioxazine chromophore are bonded with an acyl radical, an aminocarbonyl radical, a sulfonyl radical or a nitrogen-containing heteroaromatic radical.

The object of the present invention was to provide a process for the preparation of triphendioxazine dyestuffs which overcomes the disadvantages of the prior art in respect of yield and product quality.

Another object of the present invention was to provide an advantageous method for the preparation of triphendioxazines amidated on both sides.

Another object of the invention was to provide novel triphendioxazine dyestuffs, in particular those having a violet or reddish-tinged blue shade.

It has been found that the objects mentioned are achieved, surprisingly, by reduction of the triphendioxazine chromophore, which is optionally already amidated on one side, to the leuco form, amidation at the stage of the leuco form and reoxidation.

The invention relates to a process for the preparation of triphendioxazine compounds of the formula (1)

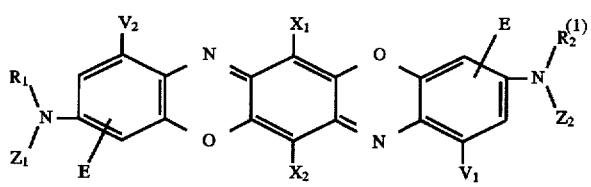

in which

R$_1$ is hydrogen or C$_1$–C$_4$-alkyl, which can be substituted by 1 or 2 substituents from the series consisting of hydroxyl, C$_1$–C$_4$-alkoxy, sulfato or sulfo;

R$_2$ has one of the meanings of R$_1$;

E is sulfo, carboxyl, C$_1$–C$_4$-alkylsulfonyl or a radical SO$_2$Y, in which Y is vinyl or CH$_2$CH$_2$V, in which V is hydroxyl, or is a leaving group from the series consisting of sulfato, phosphato, thiosulfato or halogen, such as chlorine;

or is —SO$_2$NR$_3$R$_4$ or —CONR$_3$R$_4$, in which

R$_3$ is hydrogen, phenyl, or C$_1$–C$_4$-alkyl, which can be substituted by hydroxyl, carboxyl, sulfo, sulfato or a radical SO$_2$Y, R$_4$ has one of the meanings of R$_3$, or, together with R$_3$ and N, forms a 5- or 6-membered heterocyclic radical, which can be interrupted by 1 to 3 further heteroatoms from the series consisting of N, O and S;

X$_1$ is halogen, such as chlorine or bromine, in particular chlorine, hydrogen, C$_1$–C$_6$-alkyl, such as methyl, ethyl or isopropyl, phenyl, phenoxy or C$_1$–C$_4$-alkoxy;

X$_2$ has one of the meanings of X$_1$;

V$_1$ is hydrogen, sulfo, methoxy, methyl or halogen, such as chlorine;

V$_2$ has one of the meanings of V$_1$; and

Z$_1$ and Z$_2$ are identical or different and are an acyl radical, an unsubstituted, alkylated or arylated aminocarbonyl radical, a sulfonyl radical or a nitrogen-containing heteroaromatic radical, which comprises reducing a compound of the formula (2)

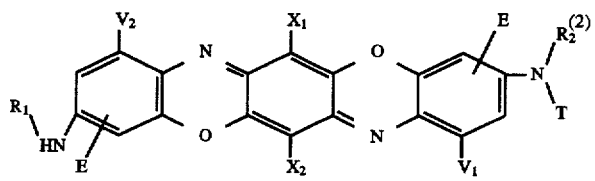

in which T is hydrogen, Z$_1$ or Z$_2$, to give a compound of the formula (3)

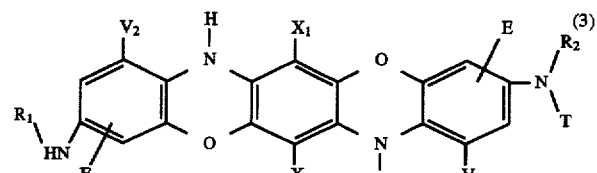

reacting this with a reactive derivative on which the radical Z$_1$ and/or Z$_2$ is based, to give a compound of the formula (4)

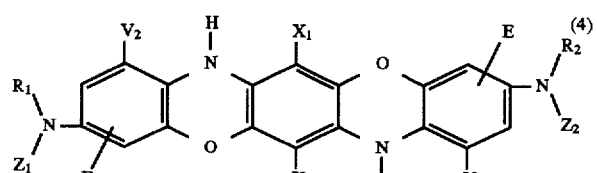

and subsequently oxidizing this to give the triphendioxazine compound of the formula (1).

It is known from Bull. Chem. Soc. Jpn. 56 (1983), 1482 that 9,13-dichlorotriphendioxazines can be dehalogenated in the 9- and 13-positions with tin in polyphosphoric acid. However, instead of the dehalogenation expected from knowledge of the prior art, surprisingly, a reduction to the leuco base takes place if the reaction according to the invention is carried out in an aqueous medium in the presence of reducing agents. The reduction is completely reversible, and the triphendioxazine color base is obtained again by oxidation.

E is preferably sulfo, —SO$_2$—CH$_2$CH$_2$—OSO$_3$M, —SO$_2$—=CH$_2$, —SO$_2$—CH$_2$CH$_2$Cl or —SO$_2$-CH$_2$CH$_2$OH.

X$_1$ and X$_2$ are preferably chlorine.

V$_1$ is preferably hydrogen.

V$_2$ is preferably hydrogen or sulfo, in particular hydrogen.

R$_1$ and R$_2$ are preferably hydrogen.

R$_3$ is preferably hydrogen, methyl or phenyl.

The radicals Z$_1$ and Z$_2$ are preferably C$_1$-C$_6$-alkylcarbonyl, C$_2$-C$_4$-alkenylcarbonyl, C$_6$-arylcarbonyl, aminocarbonyl, C$_1$-C$_6$-alkylaminocarbonyl, di-(C$_1$-C$_6$)-alkylaminocarbonyl, C$_6$-arylaminocarbonyl or C$_6$-arylsulfonyl, in which the alkyl and aryl radicals can be substituted by 1 to 3, preferably 1, identical or different substituents from the series consisting of SO$_2$Y, sulfo, carboxyl, hydroxyl, C$_1$-C$_4$-alkoxy, C$_1$-C$_4$-alkyl, cyano, halogen, acylamino, such as acetylamino, and nitro.

In the case where Z$_1$ and/or Z$_2$ are a nitrogen-containing heterocyclic radical, heterocycles from the series consisting of the triazines, pyrimidines and quinoxalines are preferred.

Particularly preferred radicals here are those of the formulae (5a) to (5d)

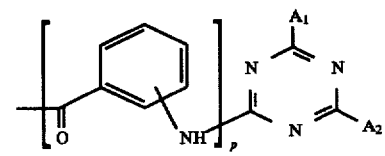 (5a)

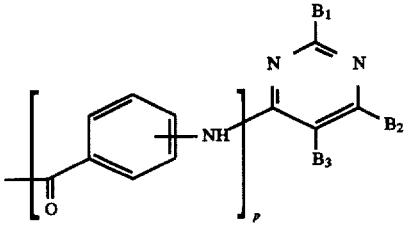 (5b)

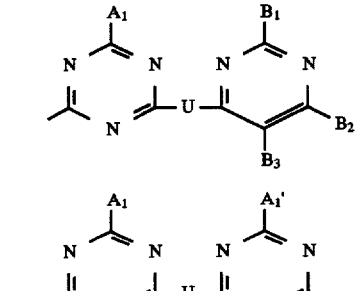 (5c)

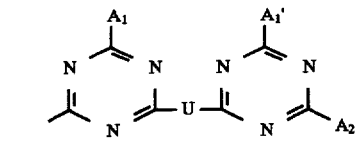 (5d)

in which p is 0 or 1, preferably 0;

A$_1$ is chlorine, fluorine, C$_1$-C$_4$-alkoxy, phenoxy, hydroxyl, amino, cyanamino or pyridinyl which is optionally substituted by carboxyl or aminocarbonyl, or a radical NR$_7$R$_8$, wherein R$_7$ is hydrogen, C$_1$-C$_4$-alkyl, which can be substituted by 1 or 2, preferably 1, identical or different substituents from the series consisting of hydroxyl, sulfo, sulfato and carboxyl, or phenyl, which can be substituted by 1 to 3 identical or different substituents from the series consisting of methoxy, methyl, halogen, sulfo or carboxyl, R$_8$ is hydrogen or C$_1$-C$_4$-alkyl, which can be substituted by 1 to 2, preferably 1, substituents from the series consisting of hydroxyl, sulfo, sulfato and carboxyl, or R$_7$ and R$_8$, together with the N atom, form a saturated 5- to 7-membered heterocyclic radical, which can also contain 1 or 2 others of the hetero groups N, O, S and/or SO$_2$, for example piperidine, morpholine, pyrrolidine, piperazine, thiomorpholine or thiomorpholine dioxide, in particular morpholine;

A$_2$ has one of the meanings of A$_1$ and is, in particular, chlorine, fluorine or cyanoamino;

A$_1$' has one of the meanings of A$_1$;

U is a bridge member from the series consisting of —NH—C$_1$-C$_6$-alkylene-NH—, —NH—C$_6$-arylene-NH—, in which arylene can be substituted by 1 or 2 sulfo, carboxyl, methyl and/or methoxy radicals,

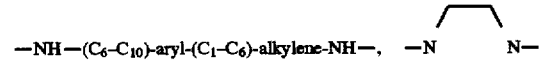

and

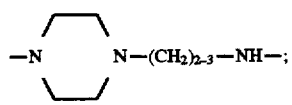

B$_1$ is hydrogen, chlorine, fluorine, trichloromethyl, trifluoromethyl or methylsulfonyl;

B$_2$ is hydrogen, chlorine, methyl, methylsulfonyl or fluorine; and

B$_3$ is hydrogen, cyano, fluorine or chlorine, with the proviso that at least one of the radicals B$_1$ or B$_2$ is a leaving group from the series consisting of chlorine, fluorine and methylsulfonyl.

The bridge member U is particularly preferably a radical of the formula

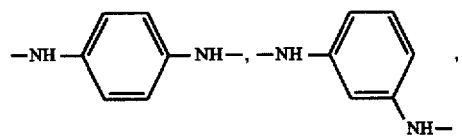

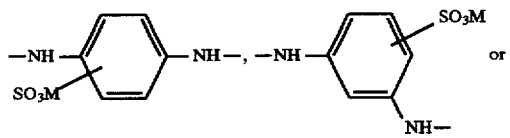 or

The abovementioned radical NR$_7$R$_8$ is particularly preferably a structure of the formulae (6a) to (6d)

 (6a)

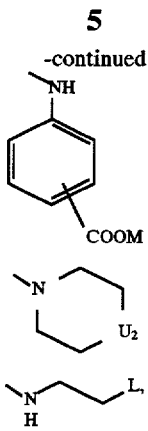

(6b)

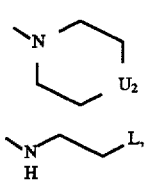

(6c)

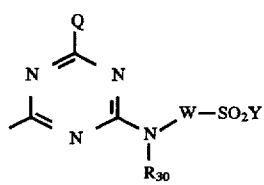

(6d)

in which

U$_2$ is a chemical bond, —CH$_2$—, —O—, —NH—, >N—(CH$_2$)$_2$OH, —S— or —SO$_2$—;

y is 1 or 2;

M is hydrogen or an alkali metal, such as Li, Na or K, and

L is hydroxyl, sulfo, sulfato or carboxyl.

Z$_1$ and Z$_2$ furthermore preferably represent a fiber-reactive radical of the formula (5e)

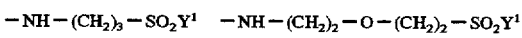

(5e)

in which

Q is halogen, such as chlorine or fluorine, hydroxyl, cyanoamino or a radical NR$_{30}$—W—SO$_2$Y;

W is C$_2$–C$_6$-alkylene, which can be interrupted by a hetero group O, S, NH or SO$_2$; phenylene, which can be substituted by methoxy or sulfo; or aralkylene, such as —CH$_2$-phenylene or -phenylene-CH$_2$—;

R$_{30}$ is hydrogen, C$_1$–C$_4$-alkyl, phenyl, which can be substituted by a sulfo group, or the radical —W$_1$—SO$_2$Y, in which W$_1$ is C$_2$–C$_6$-alkyl, and Y has one of the abovementioned meanings.

Particularly preferably, W is —(CH$_2$)$_2$—, —(CH$_2$)$_3$—, —(CH$_2$)$_2$—O—(CH$_2$)$_2$—, 1,4-phenylene or 1,3-phenylene and R$_{30}$ is hydrogen, methyl or phenyl.

The radical NR$_{30}$—W—SO$_2$Y is particularly preferably one of the formulae defined below

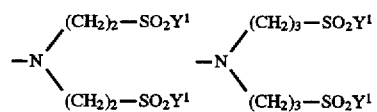

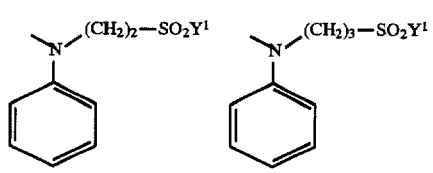

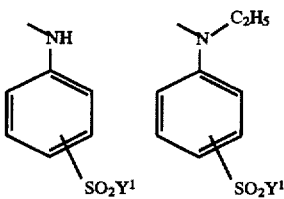

in which

Y$^1$ is vinyl, β-hydroxyethyl, β-chloroethyl or β-sulfatoethyl.

Particularly preferred radicals Z$_1$ and Z$_2$ are

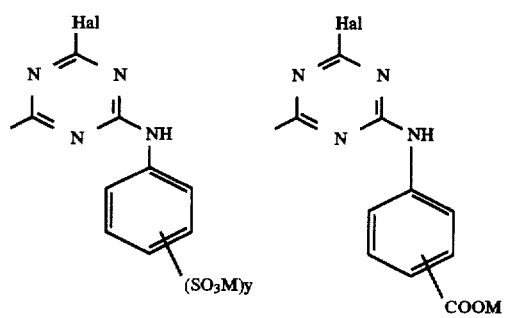

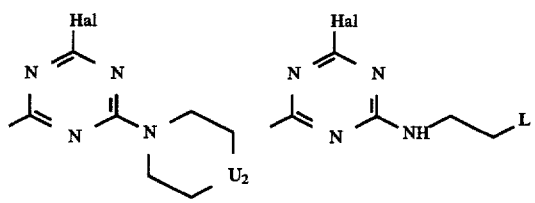

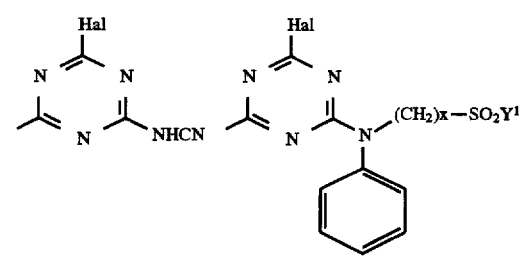

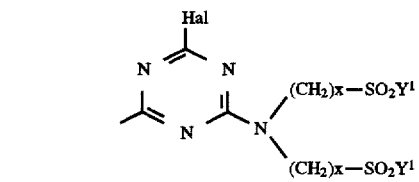

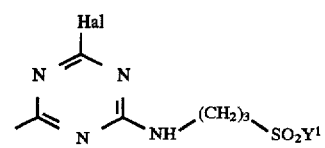

-continued

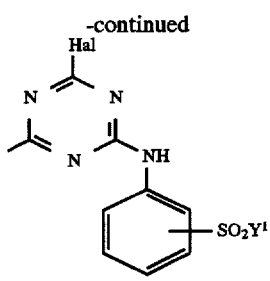

in which x is 2 or 3;

y is 1 or 2;

$U_2$ has one of the abovementioned meanings;

L is hydroxyl, sulfo, carboxyl or sulfato;

$Y^1$ has one of the abovementioned meanings;

Hal is chlorine or fluorine, and

M is hydrogen or an alkali metal.

Examples of the radical $NR_{30}$—W—$SO_2Y$ are
N-phenyl-3-(β-sulfatoethylsulfonyl)-propylamino,
N-methyl-2-(β-sulfatoethylsulonnyl)-ethylamino,
N-phenyl-2-(β-sulfatoethylsulfonyl)-ethylamino,
3-(β-sulfatoethylsulfonyl)-propylamino,
bis-{3-(β-sulfatoethylsulfonyl)-propyl}-amino,
bis-{2-(β-sulfatoethylsulfonyl)-ethyl}-amino,
bis-{3-(β-chloroethylsulfonyl)-propyl}-amino,
bis-{2-(β-chloroethylsulfonyl)-ethyl}-amino,
N-phenyl-3-(vinylsulfonyl)-propylamino,
N-phenyl-2-(vinylsulfonyl)-ethylamino, 3-(vinylsulfonyl)-propylamino,
bis-{3-(vinylsulfonyl)-propyl}-amino, bis-{2-(vinylsulfonyl)-ethyl}-amino,
3-(β-sulfatoethylsulfonyl)-phenylamino,
4-(β-sulfatoethylsulfonyl)-phenylamino,
2-methoxy-5-(β-sulfatoethylsulfonyl)-phenylamino,
2,5-dimethoxy-4-(β-sulfatoethylsulfonyl)-phenylamino and
2-methoxy-5-methyl-4-(β-sulfatoethylsulfonyl)-phenylamino.

Examples of radicals of the formula $Z_1$ and/or $Z_2$ are
phenylsulfonyl, 4-methylphenylsulfonyl, 4-acetylaminosulfonyl,
phenylaminocarbonyl, aminocarbonyl, benzoyl, 2-carboxybenzoyl,
4-carboxybenzoyl, 3-(β-chloroethylsulfonyl)-benzoyl, 3-nitrobenzoyl,
4-nitrobenzoyl, acetyl, propionyl, 2-carboxy-acryloyl, 2-carboxy-propionyl,
2,4-dichloro-triazin-6-yl, 2-(2'-sulfophenyl)amino-4-chloro-triazin-6-yl,
2-(3'-sulfophenyl)amino-4-chloro-triazin-6-yl,
2-(4'-sulfophenyl)amino-4-chloro-triazin-6-yl,
2-(2',5'-disulfophenyl)amino-4-chloro-triazin-6-yl,
2-cyanoamino-4-chloro-triazin-6-yl, 2-phenoxy-4-chloro-triazin-6-yl,
2-methoxy-4-chloro-triazin-6-yl, 2-amino-4-chloro-triazin-6-yl,
2-(β-sulfoethyl)amino-4-chloro-triazin-6-yl,
2-(N-β-sulfoethyl-N-methyl-)amino-4-chloro-triazin-6-yl,
2-(β-sulfoethyl)amino-4-fluoro-triazin-6-yl,
2-(N-β-sulfoethyl-N-methyl-)amino-4-fluoro-triazin-6-yl,
bis-{2,4-(β-sulfoethyl)amino}-triazin-6-yl,
bis-{2,4-(β-hydroxyethyl)amino}-triazin-6-yl, 2,4-dicyanoamino-triazin-6-yl,
2-(β-sulfoethyl)amino-4-cyanoamino-triazin-6-yl,
4-fluoro-2-{N-phenyl-2'-(β-sulfatoethyl)sulfonyl-ethyl-amino}-triazin-6-yl,
4-fluoro-2-{N-phenyl-3'-(β-sulfatoethyl)sulfonyl-propyl-amino}-triazin-6-yl,
4-fluoro-2-{N-methyl-2'-(β-sulfatoethyl)sulfonyl-ethyl-amino}-triazin-6-yl,
4-fluoro-2-{3'-(β-sulfatoethyl)sulfonyl-propyl-amino}-triazin-6-yl,
4-chloro-2-{N-phenyl-2'-(β-sulfatoethyl)sulfonyl-ethyl-amino}-triazin-6-yl,
4-chloro-2-{N-phenyl-3'-(β-sulfatoethyl)sulfonyl-propyl-amino}-triazin-6-yl,
4-chloro-2-{N -methyl-2'-(β-sulfatoethyl)sulfonyl-ethyl-amino}-triazin-6-yl,
4-chloro-2-{3'-(β-sulfatoethyl)sulfonyl-propyl-amino}-triazin-6-yl,
4-cyanoamino-2-{N-phenyl-2'-(β-sulfatoethyl)sulfonyl-ethyl-amino}-triazin-6-yl,
4-cyanoamino-2-{N-phenyl-3'-(β-sulfatoethyl)sulfonyl-propyl-amino}-triazin-6-yl,
4-chloro-2-{4'-(β-sulfatoethyl)sulfonyl-phenyl-amino}-triazin-6-yl,
4-cyanoamino-2-{4'-(β-sulfatoethyl)sulfonyl-phenyl-amino}-triazin-6-yl,
4-chloro-2-{3'-(β-sulfatoethyl)sulfonyl-phenyl-amino}-triazin-6-yl,
4-cyanoamino-2-{3'-(β-sulfatoethyl)sulfonyl-phenyl-amino}-triazin-6-yl,
4-chloro-2-{2'-methoxy-5'-(β-sulfatoethyl)sulfonyl-phenyl-amino}-triazin-6-yl
4-cyanoamino-2-{2'-methoxy-5'-(β-sulfatoethyl)sulfonyl-phenyl-amino}-triazin-6-yl,
4-fluoro-2-{4'-(β-sulfatoethyl)sulfonyl-phenyl-amino}-triazin-6-yl,
4-fluoro-2-{4'-(β-sulfatoethyl)sulfonyl-phenyl-amino}-triazin-6-yl,
2,4-difluoro-pyrimidin-6-yl, 2,4-difluoro-5-chloro-pyrimidin-6-yl,
2,4,5-trichloro-pyrimidin-6-yl, 2-fluoro-5-chloro-pyrimidin-6-yl,
5-cyano-2,4-dichloro-pyrimidin-6-yl, 2-methylsulfonyl-4-methyl-5-chloro-pyrimidin-6-yl, 2-fluoro-4-methyl-5-chloro-pyrimidin-6-yl, 5-chloro-4-fluoropyrimidin-6-yl,
4,5-difluoro-2-trifluormethyl-pyrimidin-6-yl, 2,5-dichloro-4-fluoro-pyrimidin-6-yl,
2-fluoro-4,5-dichloro-pyrimidin-6-yl, 4-fluoropyrimidin-6-yl, 2-fluoropyrimidin-6-yl, and
2-fluoro-5-chloro-pyrimidin-6-yl.

In the process according to the invention for the preparation of the triphendioxazine compounds of the formula (1) mentioned, which are amidated on both sides, the compound of the formula (2) is first reduced to give the compound of the formula (3). The reduction can be carried out with hydrogen in the presence of a catalyst, such as palladium, platinum or nickel, at temperatures of 40° to 90° C., or by non-noble metals, such as tin or zinc, in the presence of an acid, preferably a mineral acid, such as, for example, hydrochloric acid or sulfuric acid, at temperatures of 10° to 50° C. Preferably, the reduction is carried out with sodium dithionite in water, in particular at pH values of 6 to 9, preferably 6.5 to 7.5, and temperatures of 15° to 45° C., preferably 20° to 30° C.

The reducing agent is expediently employed in a 2- to 6-fold molar amount, based on the compounds of the formula (2).

The compounds of the formula (3) are novel and the invention likewise relates to them.

The compounds of the formula (3) are stable in air in an acidic medium and can be isolated as solids by filtration with suction. In a neutral medium, the process is expediently carried out under an inert gas, for example a nitrogen atmosphere.

The compounds of the formula (3) thus obtained are reacted with a corresponding amidation component under an inert gas atmosphere in water, in a solvent, such as dimethylformamide, dimethylacetamide or N-methylpyrrolidone, or in a water/solvent mixture, or in water containing auxiliaries, such as, for example, ε-caprolactam, urea, surfactants, solvents of the abovementioned type and other water-miscible solvents, such as acetone or methyl ethyl ketone, to give compounds of the formula (4), the radicals $Z_1$ and/or $Z_2$ defined above being introduced. The said amidation components are compounds from the series consisting of organic or inorganic acid halides, such as carboxylic acid or sulfonic acid chlorides, anhydrides, such as carboxylic acid or sulfonic acid anhydrides, isocyanates, carbonic acid esters, such as chlorocarbonic acid esters or carbonic acid diesters, ureas, carbamic acid chlorides, carboxylic acid esters, sulfonic acid esters and electron-depleted N-containing heterocyclic compounds which contain leaving groups, such as, in particular, halotriazines or halopyrimidines.

In the case where the amidation component is a carboxylic acid chloride, the reaction is advantageously carried out at pH values of 3 to 9, preferably 4 to 8, and temperatures of 0° to 80° C., preferably 20° to 50° C. Carboxylic acid chlorides are, for example, benzoyl chloride, 3- or 4-nitrobenzoyl chloride, chloroacetyl chloride, acetyl chloride, propionyl chloride or 3-(β-chloroethylsulfonyl)-benzoyl chloride.

In the case where the amidation component is an acid anhydride, the reaction is advantageously carried out at pH values of 3 to 9, preferably 4 to 8, and temperatures of 30° to 100° C., preferably 40° to 60° C.

Carboxylic acid anhydrides are, for example, acetic anhydride or cyclic carboxylic acid anhydrides, such as, in particular, succinic anhydride, maleic anhydride or phthalic anhydride.

In the case where the amidation component is urea or a urea derivative, the reaction is advantageously carried out in the urea (derivative) melt or in a high-boiling solvent, such as N-methylpyrrolidone or dimethylacetamide, at temperatures of 120° to 180° C.

In the case where the amidation component is a carbamic acid chloride, such as Cl—CO—NHC$_2$H$_5$, the reaction is advantageously carried out in water at pH values of 4 to 7 and temperatures of 40° to 95° C.

In the case where the amidation component is a carboxylic acid ester, such as ethyl acetate, the reaction is advantageously carried out in water or a water/solvent mixture at temperatures of 90° to 150° C. and in the presence of acid or Lewis acid catalysts.

In the case where the amidation component is a sulfonic acid ester, such as para-methylphenyl-SO$_2$—OC$_2$H$_5$, the reaction is advantageously carried out in water at pH values of 2 to 5 and temperatures of 80° to 150° C.

In the case where the amidation component is a 2,4-difluoro-triazine compound, the reaction is advantageously carried out at pH values of 3 to 9, preferably 4 to 8, and temperatures of 0° to 60° C., preferably 0° to 40° C.

In the case where the amidation component is a 2,4-dichloro-triazine compound, the reaction is advantageously carried out at pH values of 3 to 10, preferably 4 to 8, and temperatures of 20° to 100° C., preferably 30° to 80° C.

In the case where the amidation component is a monochloro-triazine compound, the reaction is advantageously carried out at pH values of 3 to 9, preferably 4 to 8, and temperatures of 50° to 100° C., preferably 60° to 90° C.

In the case where the amidation component is a monofluoro-triazine compound, the reaction is advantageously carried out at pH values of 3 to 9, preferably 4 to 8, and temperatures of 40° to 90° C., preferably 50° to 70° C.

In the case where the amidation component is a di- or trifluoro-pyrimidine compound, the reaction is advantageously carried out at pH values of 3 to 9, preferably 4 to 8, and temperatures of 0° to 60° C., preferably 20° to 40° C.

In the case where the amidation component is a carbonic acid derivative, for example an isocyanate, a chlorocarbonic acid ester or a carbonic acid ester, the reaction is advantageously carried out at pH values of 4 to 8, preferably 5 to 7, and temperatures of 20° to 60° C., preferably 25° to 40° C.

In the case where the amidation component is a sulfonyl chloride, the reaction is advantageously carried out at pH values of 4 to 8, preferably 5 to 7, and temperatures of 20° to 60° C., preferably 25° to 40° C. Sulfonyl chlorides are, for example, 4-methylphenyl-sulfonyl chloride, phenylsulfonyl chloride or 4-(acetylamino)phenylsulfonyl chloride.

If several possibilities for the preparation of the same products are described, the reaction with acid chlorides is the preferred procedure.

The molar ratios of amounts for the preparation of compounds of the formula (4) amidated symmetrically on both sides are: compound of the formula (3) where T=H to amidation component 1:2 to 1:6, preferably 1:2 to 1:3.

Mixed condensation reactions (3)→(4) for the preparation of asymmetric dioxazines, i.e. $Z_1$ differs from $Z_2$, can be carried out by reacting the compound of the formula (2) where T=H with an approximately 1:1 mixture of the amidation components corresponding to the radicals $Z_1$ and $Z_2$. The asymmetric product is obtained here as a mixture with the two symmetric condensation products. A better and therefore preferred procedure, however, is the reaction of that compound of the formula (3) in which T=$Z_1$ with the amidation component corresponding to the radical $Z_2$. Considerably purer uniform products are obtained in this reaction than in the mixed condensation reaction, which is a particular advantage of the process variant according to the invention. For the reaction of a compound of the formula (3) where T=Z1 with the amidation component $Z_2$, the said amidation component is employed in a molar ratio of 1:1 to 1:3, preferably 1:1 to 1:2, to the compound of the formula (3).

The compounds of the formula (4) are novel and the invention likewise relates to them.

The compounds of the formula (4) are converted into the compounds of the formula (1) by oxidation. This oxidation can be carried out by atmospheric oxygen at pH values of 6 to 10, or by addition of an oxidizing agent, such as hydrogen peroxide or an alkali metal peroxodisulfate, at pH values of 4 to 7 and 20° to 60° C., preferably 25° to 40° C. The amount of oxidizing agent added is expediently 2 to 6 molar equivalents, based on the compound of the formula (4).

It is surprising that, in spite of an additional reduction and oxidation step, the process according to the invention gives considerably higher yields and better product qualities than according to the prior art.

Particularly preferred triphendioxazine compounds of the formula (1) are those of the formula (1a)

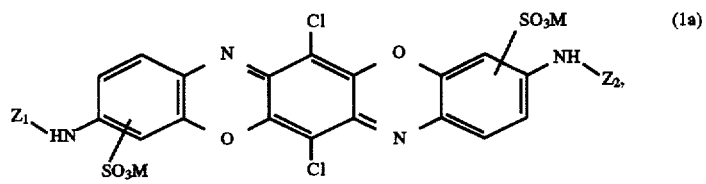

(1a)

in which M is Na, K or Li.

Particularly preferred triphendioxazine compounds of the formula (1) are those which correspond to the formula (7a)

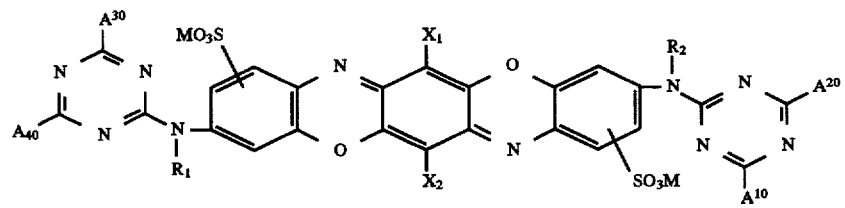

(7a)

in which

R$_1$, R$_2$, X$_1$, X$_2$ and M have one of the abovementioned meanings;

A$^{10}$ is the radical of a C$_1$–C$_4$-aliphatic amine, which can be substituted by sulfo, hydroxyl or carboxyl, or the radical of a C$_6$- or C$_{10}$-aromatic amine, which can be substituted by SO$_2$Y, 1 or 2 methoxy groups and/or 1 or 2 sulfo groups, or cyanoamino;

A$^{20}$ is halogen or has one of the meaning of A$^{10}$;

A$^{30}$ has one of the meanings of A$^{10}$; and

A$^{40}$ has one of the meanings of A$^{10}$ or is halogen.

Such dyestuffs are known in some cases from U.S. Pat. No. 5,272,267, U.S. Pat. No. 5,438,137, U.S. Pat. No. 5,456,726 and U.S. Pat. No. 5,486,607 and are suitable, for example, as reactive dyestuffs for dyeing cellulose fibers. The procedure described in the present invention is advantageous in respect of the yield and purity of these dyestuffs.

Dyestuffs of the formula (7a) in which both the radicals A$^{10}$ and A$^{30}$ are —NH-arylene-SO$_2$Y, and both the radicals A$^{20}$ and A$^{40}$ are fluorine, chlorine, —NH—(CH$_2$)$_2$—SO$_3$H or —NH-phenylene-(SO$_3$H)$_{1-2}$ or are a radical —NH-arylene-SO$_2$Y are already known from U.S. Pat. No. 5,272, 267, U.S. Pat. No. 5,438,137 and Japanese Patent Application No. 02238063, and are suitable, for example, as reactive dyestuffs are dyeing cellulose fibers. The procedure described in the present invention is particularly advantageous in respect of the yield and purity of these dyestuffs.

Dyestuffs of the formula (7a) in which both the radicals A$^{10}$ and A$^{30}$ are the radical of a sulfonated phenylamine, such as —NH-phenylene-(SO$_3$H)$_{1-2}$, and both the radicals A$^{20}$ and A$^{40}$ are fluorine or chlorine are already known from U.S. Pat. No. 3,883,523 and are suitable, for example, as reactive dyestuffs for dyeing cellulose fibers. The procedure described in the present invention is particularly advantageous in respect to the yield and purity of these dyestuffs.

Those dyestuffs of the formula (7a) in which both the radicals A$^{1*}$ and A$^{3*}$ are cyanoamino and the two radicals A$^{2*}$ and A$^{40}$ are fluorine, chlorine or are a radical of the formula

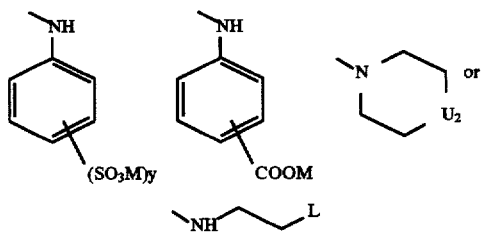

in which M, L, y and U$_2$ have one of the abovementioned meanings, are novel and the present invention therefore relates to them.

Those dyestuffs of the formula (7a) in which both the radicals A$^{10}$ and A$^{30}$ are N(aryl)—(CH$_2$)$_{2-3}$—SO$_2$Y and both radicals A$^{20}$ and A$^{40}$ are fluorine or chlorine are already known from U.S. Pat. No. 5,405,947 and U.S. Pat. No. 5,484,458 and are suitable, for example, as reactive dyestuffs for dyeing cellulose fibers. The procedure described in the present invention is particularly advantageous in respect of the yield and purity of these dyestuffs.

Particularly preferred dyestuffs of the formula (1) are furthermore those dyestuffs in which the radicals Z$_1$ and Z$_2$ have different meanings, for example the compound of the formula (7b)

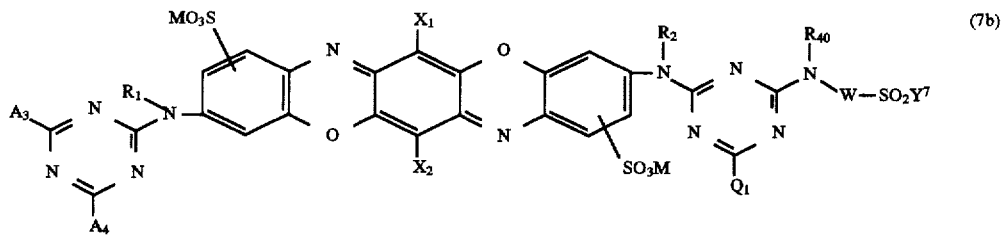
(7b)

in which $R_1, R_2, X_1, X_2$, W and M have one of the abovementioned meanings;

$R_{40}$ is hydrogen, $C_1$–$C_4$-alkyl, phenyl or sulfophenyl;

Those dyestuffs of the formula (7b) in which $Q_1$ is halogen and W is phenylene are already known in some cases from U.S. Pat. No. 5,272,267 and U.S. Pat. No. 5,438,137. The procedure described in the invention is advantageous in respect of the yield and purity of these dyestuffs.

Particularly preferred dyestuffs of the formula (1) are furthermore the asymmetric dyestuffs of the formula (7c)

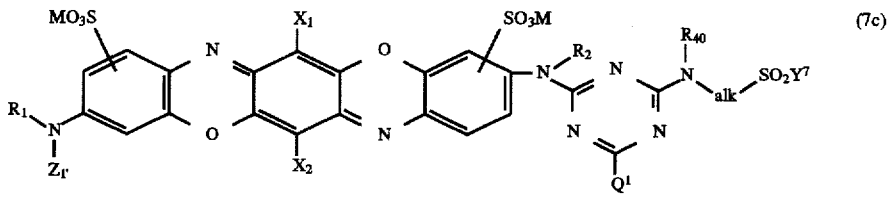
(7c)

$Q_1$ is fluorine, chlorine, amino, $C_1$–$C_4$-alkoxy, phenoxy, or pyridinyl, which can be substituted by carboxyl or aminocarbonyl, or cyanoamino;

$Y^7$ is β-sulfatoethyl, β-chloroethyl or vinyl;

$A_3$ is fluorine, chlorine, cyanoamino or amino; and $A_4$ is one of the following radicals

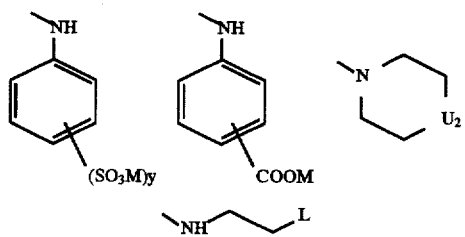

in which M, $U_2$, y and L have one of the abovementioned meanings.

Those dyestuffs of the formula (7b) in which the radical $Q_1$ is cyanoamino and at the same time W is phenylene are particularly preferred. They are novel and the invention therefore relates to them.

Those dyestuffs of the formula (7b) in which the radical W is $C_2$–$C_6$-alkylene and $Q_1$ has one of the abovementioned meanings are likewise particularly advantageous. They are novel and the invention therefore relates to them.

The dyestuffs of the formula (7b) are suitable, for example, as reactive dyestuffs for dyeing cellulose fibers.

in which $R_1$, $R_2$, $R_{40}$, $X_1$, $X_2$, $Q^1$, $Y^7$ and M have one of the abovementioned meanings;

alk is ethylene or propylene; and $Z_1'$ is $C_1$–$C_4$-alkylcarbonyl, $C_2$–$C_4$-alkenylcarbonyl, aminocarbonyl, $C_1$–$C_6$-alkylaminocarbonyl, $C_6$-arylaminocarbonyl, $C_6$-arylcarbonyl or $C_6$-arylsulfonyl, which can be substituted by hydroxyl, cyano, sulfo, sulfato, carboxyl, acetylamino or $SO_2Y^7$.

$Z_1'$ is, for example, acetyl, β-carboxyacryloyl, β-carboxypropionyl, 3-(β-chloroethylsulfonyl)-benzoyl, phenylsulfonyl, 4'-methylphenylsulfonyl, benzoyl or 2- or 4-carboxybenzoyl.

Dyestuffs of the formula (7c) are novel and the invention therefore relates to them. They are suitable, for example, as reactive dyestuffs for dyeing cellulose fibers.

Particularly preferred dyestuffs of the formula (1) are furthermore the asymmetric dyestuffs of the formula (7d)

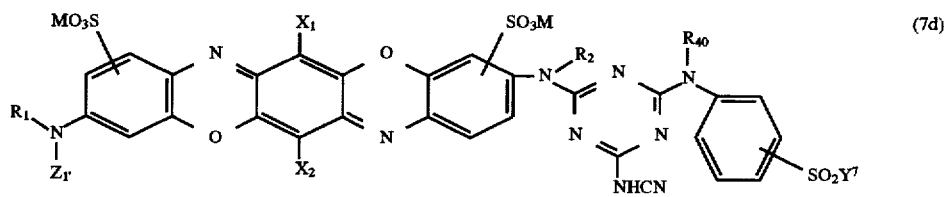
(7d)

in which $R_1$, $R_2$, $R_{40}$, $Y^7$, $Z_1'$, $X_1$, $X_2$ and M have one of the abovementioned meanings.

Dyestuffs of the formula (7d) are novel and the invention therefore relates to them. They are suitable, for example, as reactive dyestuffs for dyeing cellulose fibers.

Particularly preferred dyestuffs of the formula (1) are furthermore the asymmetric dyestuffs of the formula (7e)

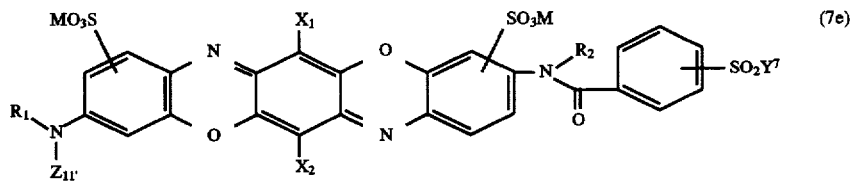
(7e)

in which

R$_1$, R$_2$, X$_1$, X$_2$, Y$^7$ and M have one of the abovementioned meanings;

Z$_{11}$' has one of the meanings of Z$_1$'; or in which Z$_{11}$' is one of the radicals

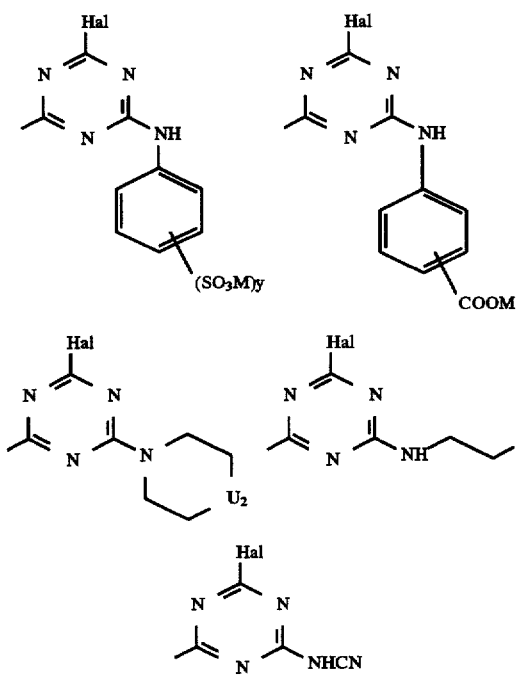

in which M, y, U$_2$, Hal and L have one of the abovementioned meanings.

Dyestuffs of the formula (7e) are novel and the invention therefore relates to them. They are suitable, for example, as reactive dyestuffs for dyeing cellulose fibers.

Particularly preferred dyestuffs of the formula (1) are, furthermore, the asymmetric dyestuffs of the formula (7f)

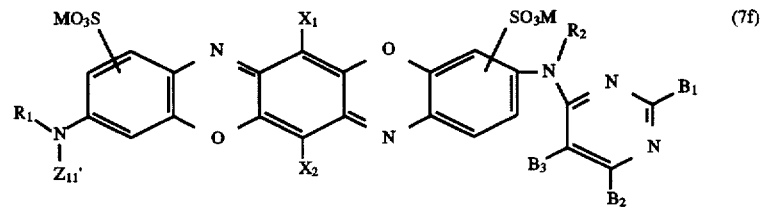
(7f)

in which

B$_1$, B$_2$, B$_3$, R$_1$, R$_2$, X$_1$, X$_2$ and M have one of the abovementioned meanings and Z$_{11}$' has one of the meanings given under (7e).

Dyestuffs of the formula (7f) are novel and the invention therefore relates to them. They are suitable, for example, as reactive dyestuffs for dyeing cellulose fibers.

Particularly preferred dyestuffs of the formula (7f) are those in which B$_1$ and B$_2$ are in each case fluorine.

The present invention therefore relates to triphendioxazine compounds of the formula (7)

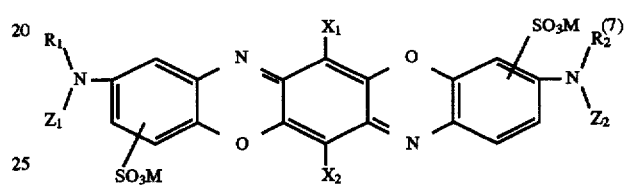
(7)

comprising the dioxazine compounds described above as novel.

The dyestuffs according to the invention are suitable for dyeing and printing fiber materials. Suitable fiber materials are cellulose fibers, such as cotton, viscose or chemically modified cellulose, polyamides, such as polyamide 6 or polyamide 6,6, or protein fibers, such as wool or silk, or blend fabrics comprising at least one of the abovementioned fiber materials, such as cotton/polyester blend fabric or cotton/polyamide blend fabric.

The dyestuffs can be applied to cellulose fibers as direct dyestuffs or reactive dyestuffs, suitable dyeing processes being exhaustion or pad-dyeing processes, such as the short-time pad-batch process or the pad-steam process, but particularly preferably exhaustion processes. The dyestuffs can be applied to polyamide or protein fibers as acid dyestuffs or reactive dyestuffs.

Dyestuffs of the formula (1) in which at least one of the radicals Z$_1$ and Z$_2$ is a reactive group from the pyrimidine series are particularly tinctorially strong and are distinguished by very good fastnesses to washing.

Accompanying white laundry is stained only very little during washing. This finding is particularly surprising, since triphendioxazines to date have only moderate fastness to washing.

The suitability of the dyestuffs according to the invention for dyeing processes in which very small amounts of salt, for example sodium chloride or sodium sulfate, are applied is likewise remarkable, amounts of salt to 50 to 80 g/l being customary in reactive dyeing, and even so-called low-salt dyestuffs in any case requiring 20 to 40 g/l of salt. A loss of tinctorial strength is usually suffered with reduced amounts of salt, i.e. for ecological reasons the dyestuffs are used for dyeing under conditions which do not correspond to their optimum. Surprisingly, it has now been found that the tinctorial strength which can be achieved for the triphendioxazines of the formula (1) according to the invention in which at least one of the radicals $Z_1$ or $Z_2$ is a reactive group from the pyrimidine series is almost independent of the amount of salt, i.e. the amount of salt employed can be reduced drastically without a loss of tinctorial strength. The invention therefore likewise relates to such a particularly ecologically advantageous dyeing process with a greatly reduced amount of salt of 0 to 20, preferably 5 to 15, grams of electrolyte salt per liter of dye solution, not taking into account alkaline electrolyte introduced by the dyeing alkali, such as, for example, sodium hydroxide or sodium carbonate, preferably at dyeing temperatures of 40° to 90° C. in the exhaustion process.

EXAMPLES

Example A 0.1 mol (58.5 g) of the triphendioxazine compound of the formula

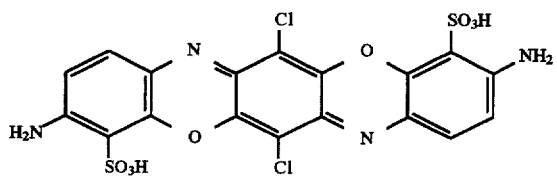

is suspended in 2 l of five molar hydrochloric acid at 25° C. under a nitrogen atmosphere for some time. A total of 20 g of tin are then added in portions in the course of 4 hours.

The mixture is subsequently stirred until the greenish-blue suspension has become completely brown, it being necessary to add further tin, if appropriate, and the batch is then filtered with suction and the residue is rinsed with one normal hydrochloric acid. The moist, greenish-brown filtercake is kept under nitrogen and is further reacted as described in the following examples.

The compound of the formula

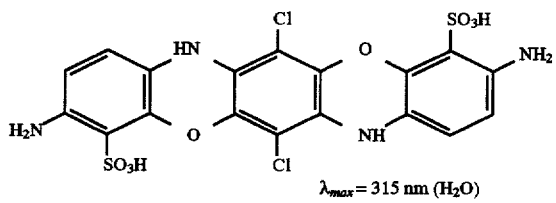

$\lambda_{max} = 315$ nm (H$_2$O)

or the hydrochloride thereof is obtained.

Example B

Alternatively, the compound from Example A can also be prepared by reacting the lithium salt of the triphendioxazine compound from Example A, prepared by dissolving the sulfonic acid with lithium hydroxide in 2.5 l of water, with 38 g of sodium dithionite at pH values of 6.5 to 7.5 and temperatures of 20° to 30° C. in a nitrogen inert gas atmosphere.

Example C

Alternatively, the compound of Example A can also be prepared by reacting the triphendioxazine compound at a temperature of 70° C. under a hydrogen pressure of 70 bar over a Raney nickel catalyst.

Example D

Alternatively, the compound of Example A can also be prepared by reacting the lithium salt of the triphendioxazine compound at a temperature of 70° C. under a hydrogen pressure of 70 bar over a palladium-on-charcoal catalyst.

Example E

Alternatively, the compound of Example A can also be prepared by reacting the triphendioxazine compound at a temperature of 20° to 30° C. in 2 liters of two normal hydrochloric acid and 25 g of zinc.

Example F 67 g of the lithium salt of the compound of the formula

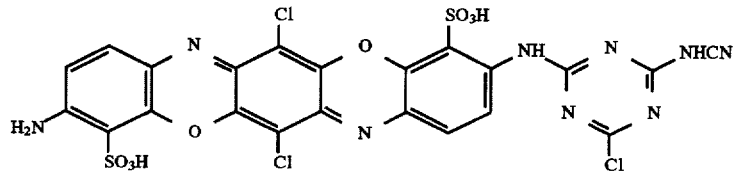

the preparation of which is described in PCT/US 94/03233, are reduced with 24 g of sodium dithionite in 2 l of water at a temperature of 25° C. and a pH of 6.5 to 7.5 to give the compound of the formula

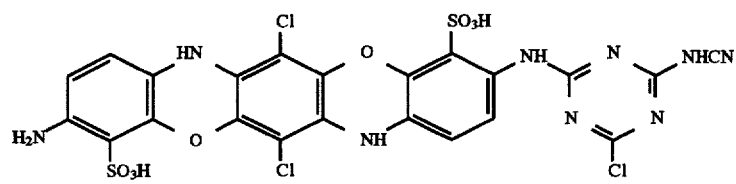

and this compound is further reacted directly, without intermediate isolation, as described in the following examples.

Example G 75.4 g of the lithium salt of the compound of the formula

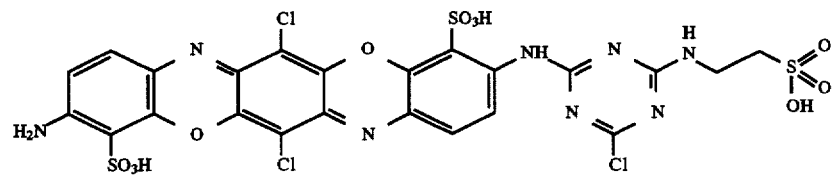

which is known from EP-A-0 385 120/Example 319 is reduced with 38 g of sodium dithionite in 1 l of water at a temperature of 25° C. and a pH of 7 to give the compound of the formula

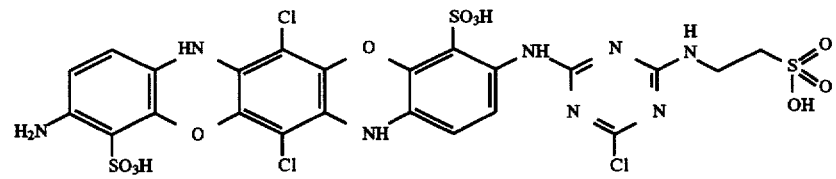

and this compound is further reacted directly, without intermediate isolation, as described in the following examples.

Example H 58.9 g of the lithium salt of the triphendioxazine compound 9,13-dichloro-3,10-diamino-4,11-disulfo-triphendioxazine are reacted with parts of acetic anhydride in 2 l of water at a pH of 7 and a temperature of 20° to 25° C. to give the compound of the formula

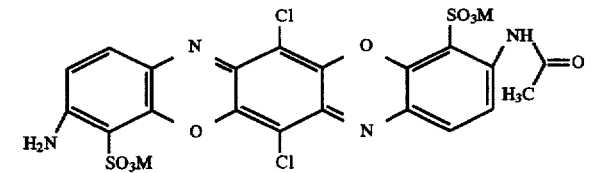

(M=Li).

This compound is reduced with 38 g of sodium dithionite at a pH of 6 to 7 and 30° C. in a nitrogen atmosphere to give a compound of the formula The mixture is subsequently stirred until the blue solution has become completely brown, and the resulting solution is then reacted further as described in the following examples.

Example I 0.1 mol (58.9 g) of the lithium salt of the triphendioxazine compound 9,13-dichloro-3,10-diamino-4,11-disulfo-triphendioxazine are reacted with 0.25 mol (37 g) of phthalic anhydride in 2 l of water at a pH of 6 to 7 and a temperature of 40° to 50° C. to give the compound of the formula

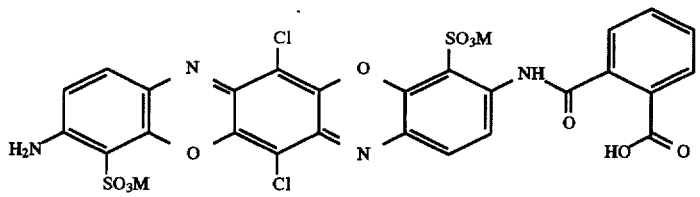

(M=Li).

This compound is reduced with 37 g of sodium dithionite at a pH of 6 to 7 and 35° C. in a nitrogen atmosphere to give a compound of the formula

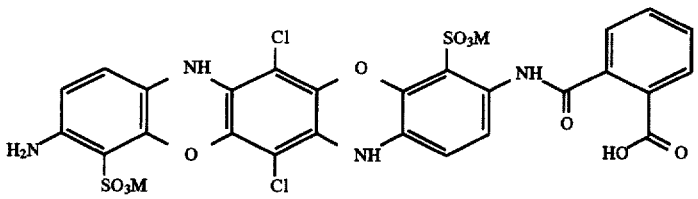

The mixture is subsequently stirred until the blue solution has become completely brown, and the resulting solution is then reacted further as described in the following examples.

The compounds mentioned in Table 1 can be prepared analogously by one of the procedures described above.

TABLE 1

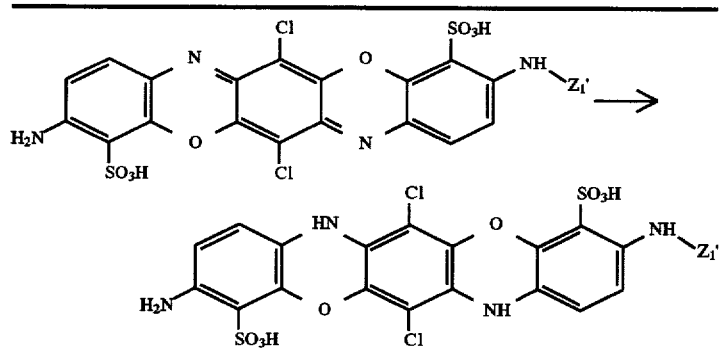

| Example | $Z_1'$ |
|---|---|
| J | 5-Chloro-2,4-difluoro-pyrimidyl |
| K | 2,4-Difluoro-pyrimidyl |
| L | Benzoyl |
| M | 3'-Nitrobenzoyl |
| N | 4'-Nitrobenzoyl |
| O | 2-Fluoro-4-(4'-sulfophenyl)amino-triazin-6-yl |
| P | 2-Chloro-4-(3'-sulfophenyl)amino-triazin-6-yl |
| Q | β-Carboxypropionyl |
| R | β-Carboxyacryloyl |
| S | 4-Chloro-2-{N-Phenyl-3'-(β-sulfatoethylsulfonyl)-propyl-amino}-triazin-6-yl |

Example T 0.1 mol (58.5 g) of the triphendioxazine compound of the formula

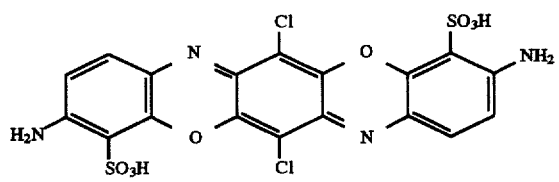

is heated at 80° to 100° C. in 1 l of 20% strength oleum for some time, and the mixture is allowed to cool and stirred on ice at 0° to 10° C. It is filtered with suction, the filtercake is suspended in water, and sodium hydroxide solution is added until a pH of 1 to 2 is reached. The mixture is then filtered with suction again and the triphendioxazine substance of the formula which is further reacted as described in the following examples, is obtained.

Example 1

0.3 mol of 2-(2'-sulfo-phenyl)-amino-4,6-dichloro-triazine is added to 0.1 mol of the leuco-dioxazine compound, prepared according to Example A, in 2 l of water at a temperature of about 60° C. and a pH of 4 to 5 and the reaction is carried out under a nitrogen atmosphere, while maintaining this pH and this temperature. The nitrogen atmosphere is then removed and stirring is continued in air until the re-oxidation is complete. The dyestuff of the formula

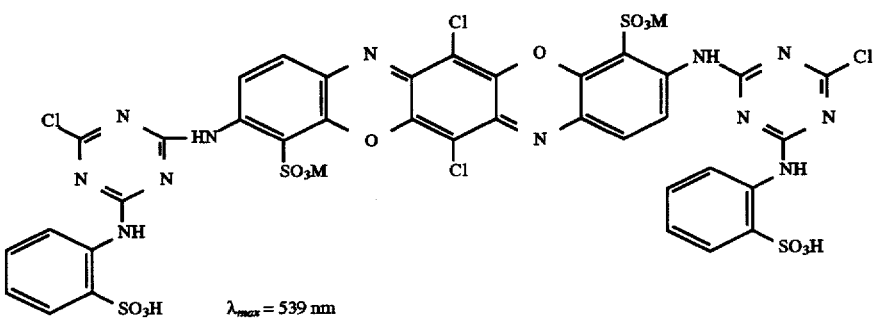

$\lambda_{max} = 539$ nm

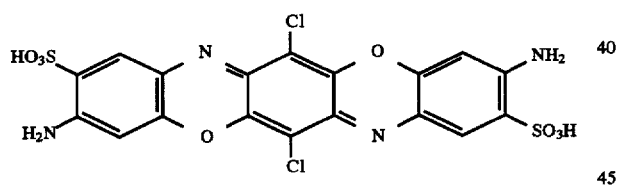

is isolated.

0.1 mol of the dioxazine compound prepared in the manner described is suspended in 2 l of five molar hydrochloric acid at 25° C. under a nitrogen atmosphere for some time. A total of 20 g of tin are then added in portions in the course of 4 hours. The mixture is subsequently stirred until the greenish-blue suspension has become completely brown, the batch is then filtered with suction and the residue is rinsed with one normal hydrochloric acid. The moist, greenish-brown filtercake is kept under nitrogen and reacted further as described in the following examples.

The compound of the formula

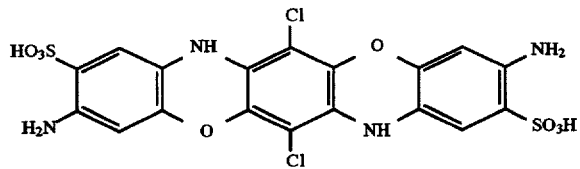

which is isolated by salting out with sodium chloride, is obtained. The dyestuff dyes cotton in intense brilliant violet color shades.

Example 2

0.25 mol of 2-(2',5'-disulfo-phenyl)-amino-4,6-dichloro-triazine is added to 0.1 mol of the leuco-dioxazine compound prepared according to Example B in 2 l of water at a temperature of about 60° C. and a pH of 4 to 5, and the reaction is carried out under a nitrogen atmosphere while maintaining the pH and temperature. The nitrogen atmosphere is then removed and the mixture is further stirred in air until the re-oxidation is complete. The dyestuff of the formula

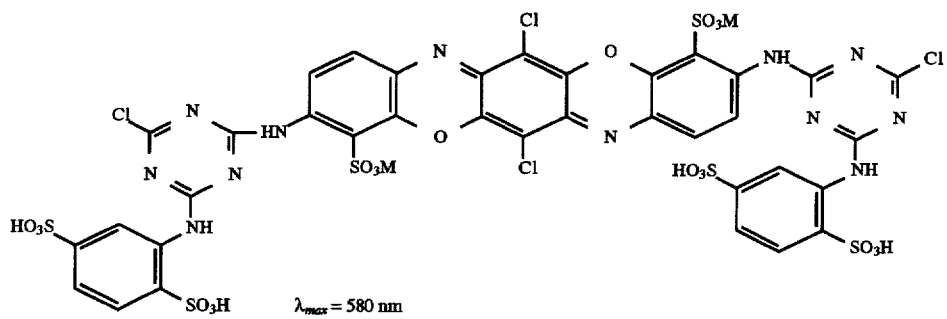

λ_max = 580 nm which is isolated by salting out with sodium chloride, is obtained. The dyestuff dyes cotton in intense brilliant violet color shades.

Example 3

0.3 mol of 2-(N-phenyl-2'-{β-sulfato-ethyl-sulfonyl}-ethyl)-amino-4,6-difluoro-triazine, known from EP-A-0 568 876, is added to 0.1 mol of the leuco-dioxazine compound prepared according to Example C in 2 l of water at a temperature of 5° to 15° C. and a pH of 4 to 5, and the mixture is stirred under a nitrogen atmosphere at pH 5 and at 30° to 40° C. until the reaction has ended. The nitrogen atmosphere is then removed and stirring is continued in air until the re-oxidation is complete. The dyestuff of the formula

Example 4

0.3 mol of 4,6-dichloro-2-cyanoamino-triazine is added to 0.1 mol of the leuco-dioxazine compound prepared according to Example A in 2 L of water at a temperature of 5° to 15° C. and a pH of 4 to 5, and the mixture is stirred under a nitrogen atmosphere at pH 5 and at 30° to 40° C. until the reaction has ended.

The nitrogen atmosphere is then removed and stirring is continued in air until the re-oxidation is complete. The dyestuff of the formula

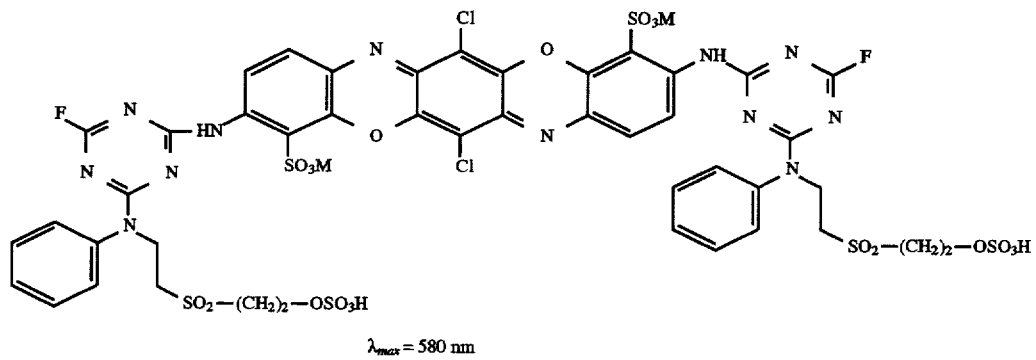

λ_max = 580 nm which is isolated by salting out with sodium chloride, is obtained. The dyestuff dyes cotton in intense brilliant reddish-tinged blue color shades.

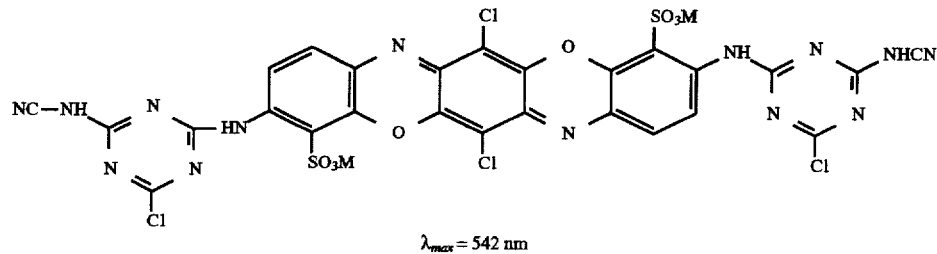

λ_max = 542 nm which is isolated from the aqueous synthesis solution by evaporation, is obtained. The dyestuff is suitable as a reactive dyestuff and/or direct dyestuff and dyes cellulose fibers, such as cotton, in intense brilliant violet color shades.

Example 5

0.05 mol of the compound from Example 4 is dissolved in 1 l of water at pH 6 and at 30° C., 0.4 mol of morpholine is added and the mixture is stirred at 60° to 70° C. and at a pH of 7 to 8 for some time until the reaction has ended. The dyestuff of the formula

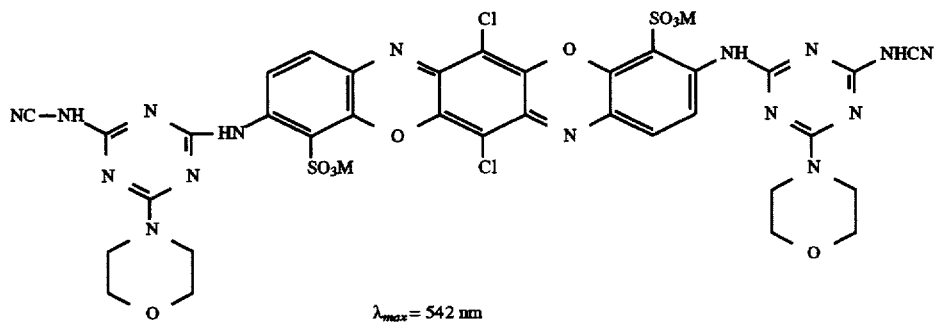

$\lambda_{max}= 542$ nm which is isolated from the aqueous synthesis solution by evaporation, is obtained. The dyestuff is suitable as a direct dyestuff and dyes cellulose fibers, such as cotton, in intense brilliant violet color shades.

Examples 6–16

Further valuable reactive dyestuffs and/or direct dyestuffs (see following Table 2) are obtained if the procedure is analogous to the abovementioned examples.

TABLE 2

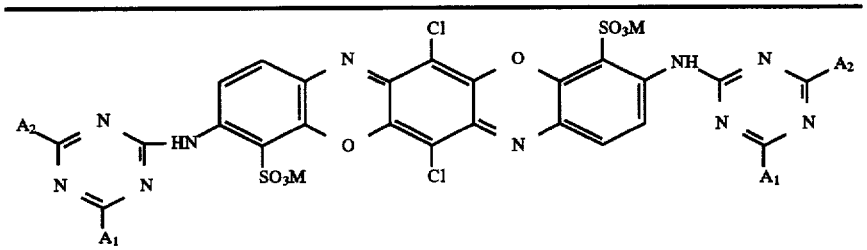

| Ex. No. | $A_1$ | $A_2$ | Color shade on cotton |
|---|---|---|---|
| 6 | 2-Carboxyphenyl | Chloro | violet (575 nm) |
| 7 | 3-Sulfophenyl | Chloro | violet (577 nm) |
| 8 | 4-Sulfophenyl | Chloro | violet (580 nm) |
| 9 | N-Phenyl-3'-(β-sulfatoethyl-sulfonyl)-propyl-amino | Fluoro | violet (581 nm) |
| 10 | Cyanoamino | Fluoro | violet (578 nm) |
| 11 | Cyanoamino | Cyanoamino | violet (579 nm) |
| 12 | Cyanoamino | N-Phenyl-3'-(β-sulfato-ethyl-sulfonyl)-propyl-amino | violet (577 nm) |
| 13 | Cyanoamino | 3-(β-Sulfatoethyl-sulfonyl)-phenyl-amino | violet (580 nm) |
| 14 | Cyanoamino | N-Methyl-β-sulfoethyl-amino | violet (578 nm) |
| 15 | Cyanoamino | β-Sulfoethyl-amino | violet (578 nm) |
| 16 | Amino | β-Sulfoethyl-amino | violet (579 nm) |
| 17 | 2-Sulfophenyl | Fluoro | violet (570 nm) |
| 18 | 2-Carboxyphenyl | Fluoro | violet (572 nm) |
| 19 | 3-Sulfophenyl | Fluoro | violet (567 nm) |
| 20 | 3-Carboxyphenyl | Fluoro | violet (570 nm) |
| 21 | 2,4-Disulfophenyl | Fluoro | violet (571 nm) |
| 22 | Morpholino | Morpholino | violet (572 nm) |
| 23 | Morpholino | β-Sulfoethylamino | violet (567 nm) |
| 24 | β-Sulfoethylamino | β-Sulfoethylamino | violet (570 nm) |
| 25 | β-Sulfoethylamino | 3-Sulfophenyl | violet (571 nm) |
| 26 | Morpholino | 4-Sulfophenyl | violet (571 nm) |
| 27 | 3-(β-Sulfatoethyl-sulfonyl)-phenylamino | Chloro | violet (578 nm) |

TABLE 2-continued

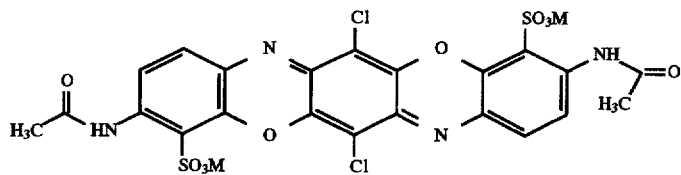

| Ex. No. | A₁ | A₂ | Color shade on cotton |
|---|---|---|---|
| 28 | 3-(β-Sulfatoethyl-sulfonyl)-phenylamino | Fluoro | violet (579 nm) |
| 29 | 3-(β-Sulfatoethyl-sulfonyl)-phenylamino | β-Sulfoethylamino | violet (579 nm) |

Example 17

0.4 mol of acetic anhydride is added to 0.1 mol of the leuco-dioxazine compound prepared according to Example A in 2 l of water at a temperature of about 40° C. and a pH of 7 under a nitrogen atmosphere and the mixture is stirred for some hours until the reaction is complete. The nitrogen atmosphere is then removed and stirring is continued in air until the re-oxidation is complete. The dyestuff of the formula

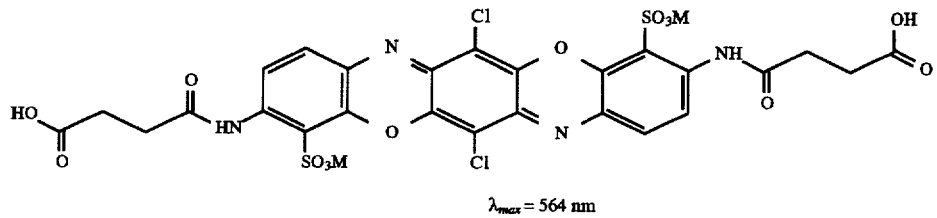

$\lambda_{max} = 564$ nm which is isolated by salting out with sodium chloride, is obtained. The dyestuff is suitable as a direct dyestuff for dyeing cotton or regenerated cellulose fibers. The dyestuff is furthermore suitable as an acid dyestuff for dyeing wool, silk or polyamide fibers, such as, in particular, polyamide 6 and polyamide 6,6. It dyes the fiber materials mentioned in intense brilliant magenta-colored color shades.

Example 18

0.4 mol of succinic anhydride is added to 0.1 mol of the leuco-dioxazine compound prepared according to Example A in 2 l of water at a temperature of 40° to 50° C. and a pH of 7 under a nitrogen atmosphere, and the mixture is stirred for some hours until the reaction is complete. The nitrogen atmosphere is then removed and stirring is continued in air until the re-oxidation is complete. The dyestuff of the formula $\lambda_{max} = 564$ nm which is isolated by salting out with sodium chloride, is obtained. The dyestuff is suitable as a direct dyestuff for dyeing cotton or regenerated cellulose fibers. The dyestuff is furthermore suitable as an acid dyestuff for dyeing wool, silk or polyamide fibers, such as, in particular, polyamide 6 and polyamide 6,6. It dyes the fiber materials mentioned in intense brilliant magenta-colored color shades. The dyestuff is furthermore suitable as a synthesis intermediate product for further dyestuffs.

Example 19

0.3 mol of 3-nitrobenzoyl chloride is added to 0.1 mol of the leuco-dioxazine compound prepared according to Example A in 4 l of water at a temperature of about 60° C. and a pH of 6 to 7 and the mixture is stirred under a nitrogen atmosphere for some time, until the reaction has ended. The nitrogen atmosphere is then removed and stirring is continued in air until the re-oxidation is complete. The dyestuff of the formula at pH 6 in the course of 1 hour and the mixture is stirred further until the reaction is complete. 0.2 mol of hydrogen peroxide is then added as a 35% strength aqueous solution and the mixture is subsequently stirred in air for some time to give the compound of the formula

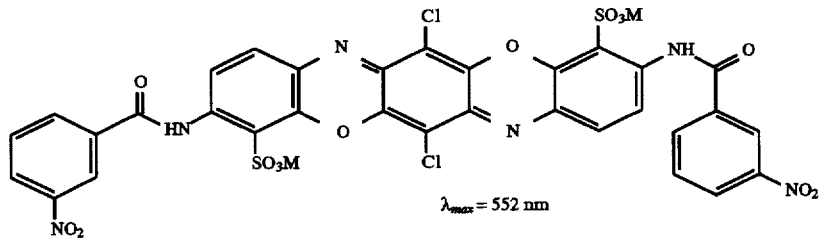

$\lambda_{max} = 552$ nm which is isolated by salting out with sodium chloride, is obtained. The dyestuff is suitable as a direct dyestuff for dyeing cotton or regenerated cellulose fibers. The dyestuff is furthermore suitable as an acid dyestuff for dyeing wool, silk or polyamide fibers, such as, in particular, polyamide 6 and polyamide 6,6. It dyes the fiber materials mentioned in intense brilliant magenta-colored color shades. The dyestuff is furthermore suitable as a synthesis intermediate product for further dyestuffs.

Further valuable direct dyestuffs and/or acid dyestuffs (see following Table 3) are obtained if the procedure is analogous to the abovementioned example.

TABLE 3

| Example No. | $Z_1'$ | $Z_2'$ | Color shade on cotton |
|---|---|---|---|
| 20 | Chloroacetyl | Chloroacetyl | magenta |
| 21 | Propionyl | Propionyl | magenta |
| 22 | 4-Nitrobenzoyl | 4-Nitrobenzoyl | magenta |
| 23 | Benzoyl | Benzoyl | magenta |
| 24 | 2-Carboxybenzoyl | 2-Carboxybenzoyl | magenta |
| 25 | 4-Carboxybenzoyl | 4-Carboxybenzoyl | magenta |
| 26 | 2-Carboxy-acryloyl | 2-Carboxy-acryloyl | magenta |

Example 27

0.22 mol of 4-acetylaminophenylsulfonyl chloride is added to 0.1 mol of the leuco compound from Example A in 2 l of water in an inert gas atmosphere at about 60° C. and

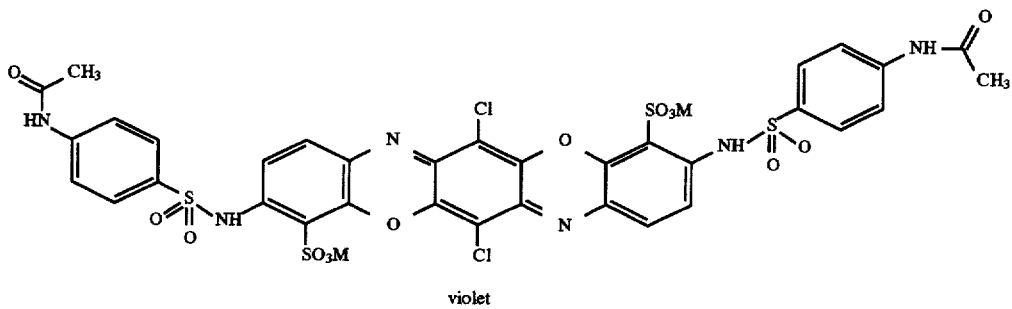

violet which is suitable as a direct dyestuff for dyeing cotton.

Example 28

0.1 mol of the dried leuco compound isolated from Example A is stirred with 7.5 mol of urea in 2 l of water in an inert gas atmosphere in the melt at about 140° C. until the reaction is complete. The reaction melt is then poured into water at 20° to 30° C., 0.2 mol of hydrogen peroxide is added as a 35% strength aqueous solution and the mixture is subsequently stirred in air for some time, until the re-oxidation is complete, to give the compound of the formula

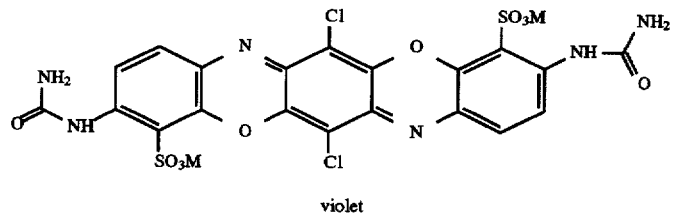

violet which is suitable as a direct dyestuff for dyeing cotton.

Example 29

0.4 mol of acetic anhydride is added to 0.1 mol of the leuco-dioxazine compound prepared according to Example T in 2 l of water in a nitrogen atmosphere at a temperature of 30° to 35° C. and a pH of 7 and the mixture is stirred for some hours, until the reaction is complete. The nitrogen atmosphere is then removed and stirring is continued in air until the re-oxidation is complete. The dyestuff of the formula

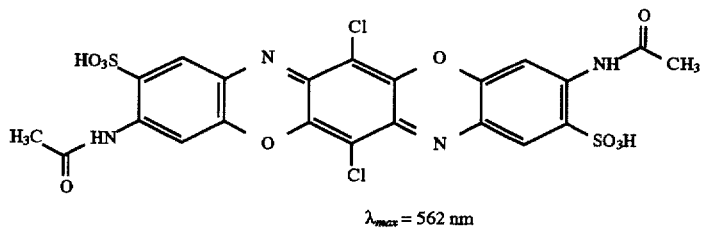

$\lambda_{max} = 562$ nm which is isolated by salting out with sodium chloride, is obtained. The dyestuff is suitable as a direct dyestuff for dyeing cotton or regenerated cellulose fibers. The dyestuff is furthermore suitable as an acid dyestuff for dyeing wool, silk or polyamide fibers, such as, in particular, polyamide 6 and polyamide 6,6. It dyes the fiber materials mentioned in intense brilliant magenta-colored color shades.

Example 30

0.12 mol of the compound 2,4-dichloro-6-(4'-{β-sulfatoethyl-sulfonyl}-phenyl)amino-triazine is added to 0.1 mol of the freshly prepared leuco compound from Example F under a nitrogen atmosphere in 2 l of water at a pH of 4 to 5 and at a temperature of 40° to 50° C. The mixture is subsequently stirred under a nitrogen atmosphere until the reaction is complete. Stirring is then continued in air at 20° to 25° C. for some time, until the re-oxidation is complete. The compound of the formula

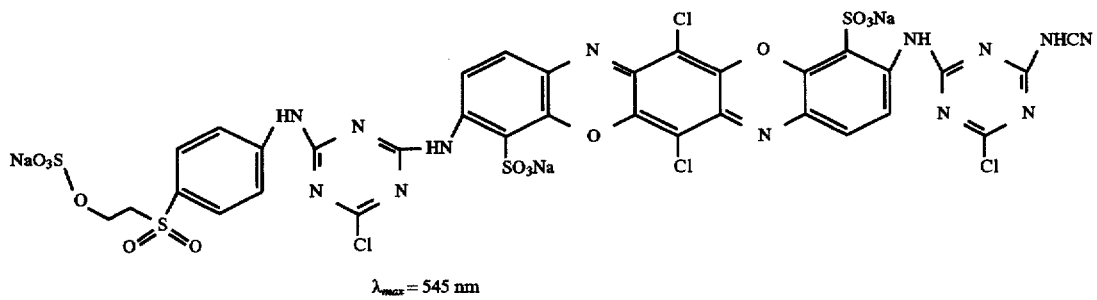

$\lambda_{max} = 545$ nm is obtained. The dyestuff is isolated from the aqueous synthesis solution by salting out with sodium chloride.

The dyestuff dyes cotton in brilliant violet color shades with good fastnesses. The dyestuff is outstandingly suitable for exhaustion dyeings, in which the salt content in the dye liquor corresponds to 10 to 30 g/l.

Example 31

0.12 mol of the compound 2,4-dichloro-6-(3'-β-sulfato-ethylsulfonyl-phenyl)amino-triazine is added to 0.1 mol of the freshly prepared leuco compound from Example G under a nitrogen atmosphere in 2 l of water at a pH of 5 to 6 and at a temperature of about 60° C. The mixture is subsequently stirred under a nitrogen atmosphere until the reaction is complete. Stirring is then continued in air at 20° to 25° C. for some time, until the re-oxidation is complete. The compound of the formula for exhaustion dyeings, in which the salt content in the liquor corresponds to 10 to 30 g/l.

Example 32

0.13 mol of the compound 2,4-dichloro-6-(N-phenyl-2'-β-sulfato-ethylsulfonyl-ethyl)-amino-triazine is added to 0.1 mol of the compound from Example G in 2 l of water at a pH of 5 to 6 and at a temperature of 50° to 60° C. The mixture is subsequently stirred under a nitrogen atmosphere until the reaction is complete. Stirring is then continued in air at 20° to 25° C. for some time, until the re-oxidation is complete. The compound of the formula

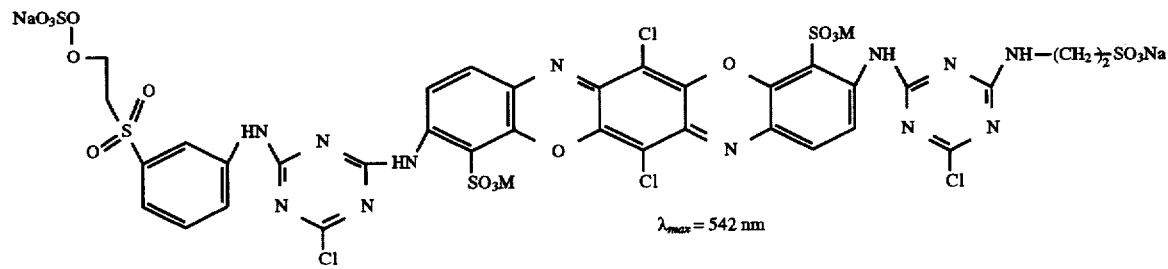

$\lambda_{max} = 542$ nm which is isolated from the aqueous synthesis solution by salting out with sodium chloride, is obtained.

The dyestuff dyes cotton in brilliant violet color shades with good fastnesses. The dyestuff is outstandingly suitable

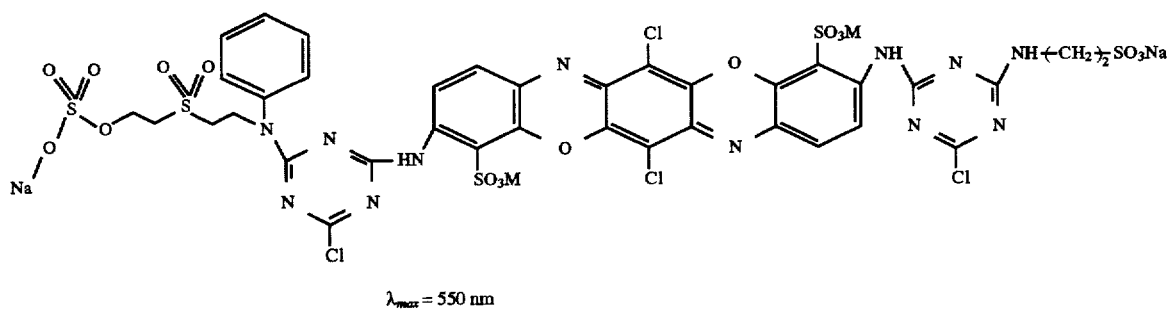

$\lambda_{max} = 550$ nm is obtained. The dyestuff is isolated from the aqueous synthesis solution by salting out with sodium chloride.

The dyestuff dyes cotton in brilliant violet color shades with good fastnesses. The dyestuff is outstandingly suitable for exhaustion dyeings, in which the salt content in the dye liquor corresponds to 10 to 30 g/l.

Example 33

0.15 mol of the compound 2,4-difluoro-6-(N-phenyl-2'-β-sulfato-ethyl-sulfonyl-ethyl)amino-triazine is added to 0.1 mol of the compound from Example G in 2 l of water at a pH of 5 to 6 and at a temperature of 0° to 10° C. The mixture is subsequently stirred under a nitrogen atmosphere, while heating at 25° C., until the reaction is complete. Stirring is then continued in air at 20° to 25° C. for some time, while maintaining the pH, until the re-oxidation is complete. The compound of the formula

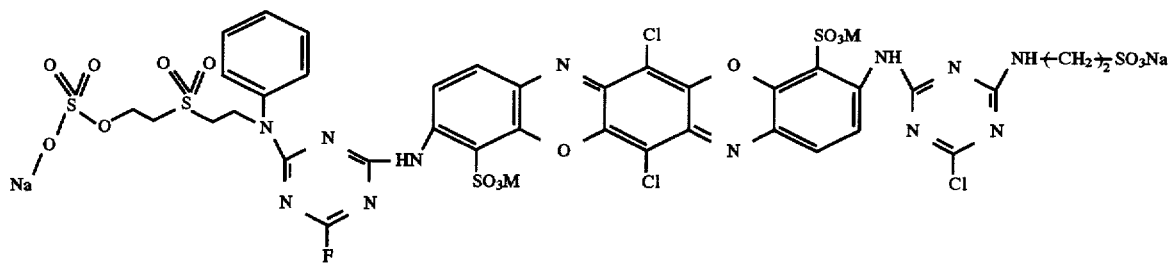

λ$_{max}$ = 548 nm is obtained. The dyestuff is isolated from the aqueous synthesis solution by salting out with sodium chloride.

The dyestuff dyes cotton in brilliant violet color shades with good fastnesses. The dyestuff is outstandingly suitable for exhaustion dyeings, in which the salt content in the dye liquor corresponds to 10 to 30 g/l.

Example 34

0.14 mol of the compound 2-chloro4-cyanoamino-6-(4'-β-sulfato-ethylsulfonyl-phenyl)amino-triazine is added to 0.1 mol of the compound from Example G in 3 l of water at a pH of 5 to 5.5 and at a temperature of 60° to 70° C. The mixture is subsequently stirred under a nitrogen atmosphere at a temperature of 70° to 800° C. and a pH of 4 to 5 until the reaction is complete. Stirring is then continued in air at 20° to 250° C. for some time, until the re-oxidation is complete. The compound of the formula

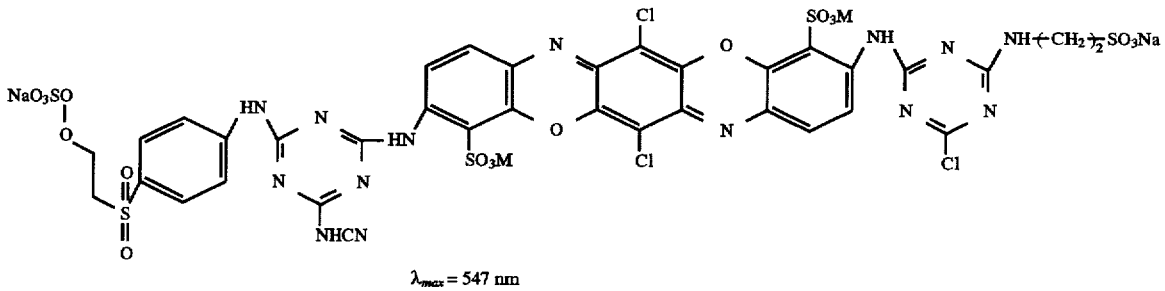

λ$_{max}$ = 547 nm is obtained. The dyestuff is isolated from the aqueous synthesis solution by salting out with sodium chloride.

The dyestuff dyes cotton in brilliant violet color shades with good fastnesses. The dyestuff is outstandingly suitable for exhaustion dyeings, in which the salt content in the dye liquor corresponds to 10 to 30 g/l.

Example 35

0.14 mol of the compound 2,4-dichloro-6-(2',5'-disulfophenyl)amino-triazine is added to 0.1 mol of the triphendioxazine dyestuff of the formula

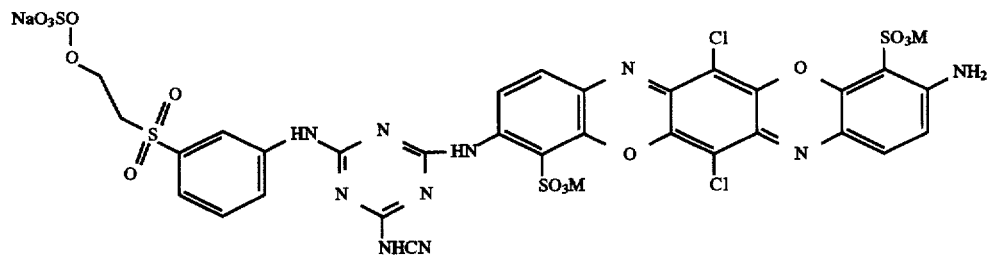

in 3 l of water at a pH of 5 to 5.5 and at a temperature of 60° to 70° C. The mixture is subsequently stirred under a nitrogen atmosphere at a temperature of 70° to 80° C. and a pH of 4 to 5 until the reaction is complete. Stirring is then continued in air at 20° to 25° C. for some time, until the re-oxidation is complete. The compound of the formula for exhaustion dyeings, in which the salt content in the dye liquor corresponds to 10 to 30 g/l.

Further valuable dyestuffs (see Table 4) are obtained if the procedure is analogous to the abovementioned examples, it being possible for the sequence of the reactions with respect to the two triazine radicals to be as desired.

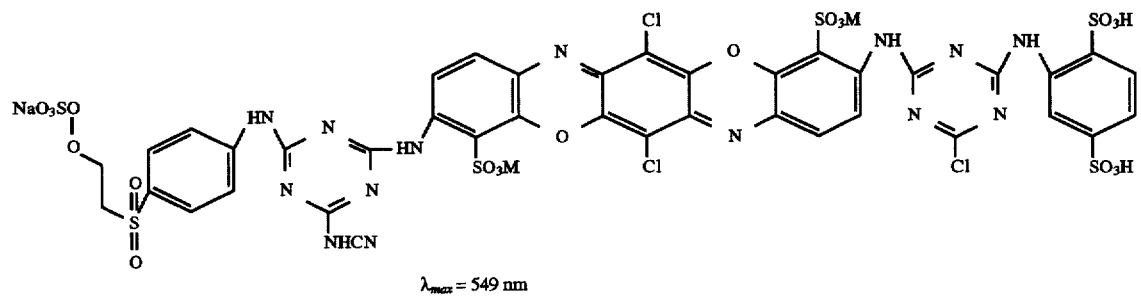

$\lambda_{max} = 549$ nm is obtained. The dyestuff is isolated from the aqueous synthesis solution by salting out with sodium chloride.

The dyestuff dyes cotton in brilliant violet color shades with good fastnesses. The dyestuff is outstandingly suitable

TABLE 4

| Ex. No. | A₁ | A₂ | A₃ | A₄ | Color shade on cotton |
|---|---|---|---|---|---|
| 36 | Chloro | Hydroxyethyl-amino | Chloro | 3-Sulfophenyl-amino | violet |
| 37 | Chloro | N-Methyl-β-sulfoethyl-amino | Chloro | 4-Sulfophenyl-amino | violet |
| 38 | Fluoro | Cyanoamino | Fluoro | Morpholino | violet |
| 39 | Chloro | Amino | Fluoro | 2,5-Disulfophenyl-amino | violet |
| 40 | Chloro | N-Phenyl-2'-(β-sulfatoethyl-sulfonyl)-ethyl-amino | Chloro | " | violet |
| 41 | Chloro | 3-(β-sulfatoethyl)-sulfonyl-phenyl-amino | Cyano amino | Cyanoamino | violet |
| 42 | Fluoro | N-Phenyl-2'-(β-sulfatoethyl-sulfonyl)-ethyl-amino | Chloro | Cyanoamino | violet |
| 43 | Chloro | 2,5-Disulfo-phenyl-amino | Fluoro | Cyanoamino | violet |
| 44 | Chloro | 2,5-Disulfo-phenyl-amino | Fluoro | N-Phenyl-2'-(β-sulfatoethyl-sulfonyl)-ethyl-amino | violet |
| 45 | Chloro | " | Chloro | 4-(β-sulfatoethyl)-sulfonyl-phenyl-amino | violet |

Example 46

0.12 mol of the compound N-phenyl-2,4-dichloro-6-{2'-β-sulfato-ethylsulfonyl-ethyl}-amino-triazine is added to 0.1 mol of the freshly prepared leuco compound from Example H in 2 l of water at a pH of 4 to 5 and at a temperature of 20° to 27° C. The mixture is subsequently stirred under a nitrogen atmosphere until the reaction is complete. Stirring is then continued in air at 20° to 25° C. for some time, until the re-oxidation is complete. The compound of the formula C. The reaction is carried out at to 60° C. and a pH of 7 and the mixture is subsequently stirred under a nitrogen atmosphere until the reaction is complete. Stirring is then continued in air at 20° to 25° C., with the addition of 0.1 mol of potassium peroxodisulfate, for some time, until the re-oxidation is complete. The compound of the formula

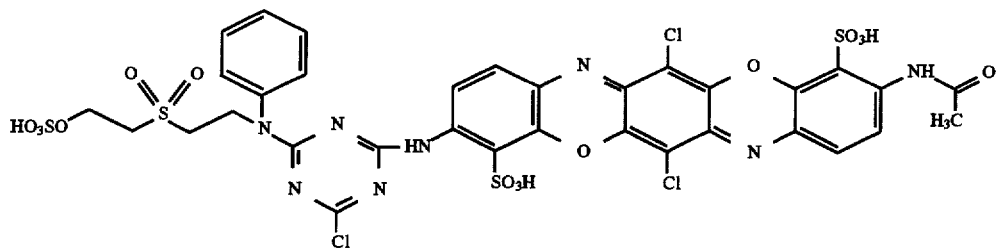

$\lambda_{max} = 533$ nm is obtained. The dyestuff is isolated from the aqueous synthesis solution by salting out with sodium chloride.

The dyestuff dyes cotton in brilliant violet color shades with good fastnesses. The dyestuff is outstandingly suitable for exhaustion dyeings, in which the salt content in the dye liquor corresponds to 10 to 30 g/l.

Example 47

The dyestuff from Example 46 is likewise obtained if 0.15 mol of cyanuric chloride, metered in as a solution in acetone, is added to 0.1 mol of the compound from Example H in 3 l of water at a pH of 6 to 7 and at a temperature of 20° to 30° C., and the mixture is subsequently stirred at 40° C. and pH 7 for some time, until the reaction has ended. 0.15 mol of N-phenyl-(2-β-sulfato-ethylsulfonyl)-ethyl-amine is then added at pH 5 and the mixture is subsequently stirred under a nitrogen atmosphere at pH 5 and about 50° C. for some time, until the reaction has ended. The dyestuff is then re-oxidized as described above and isolated as in Example 46.

Example 48

0.15 mol of succinic anhydride is added to 0.1 mol of the triphendioxazine dyestuff of the formula

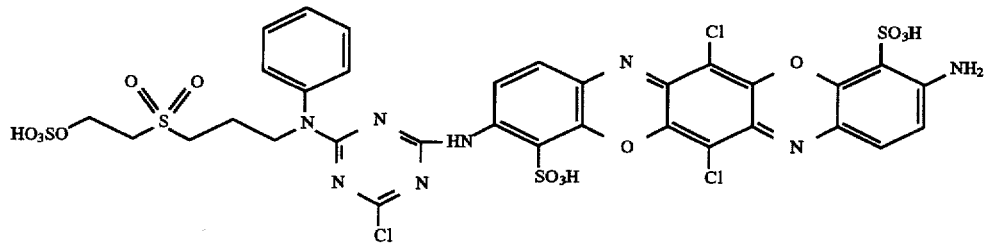

which is known from EP-A1-0 628 606, Example 1, in 2 l of water at a pH of 6 to 7 and at a temperature of 30° to 40°

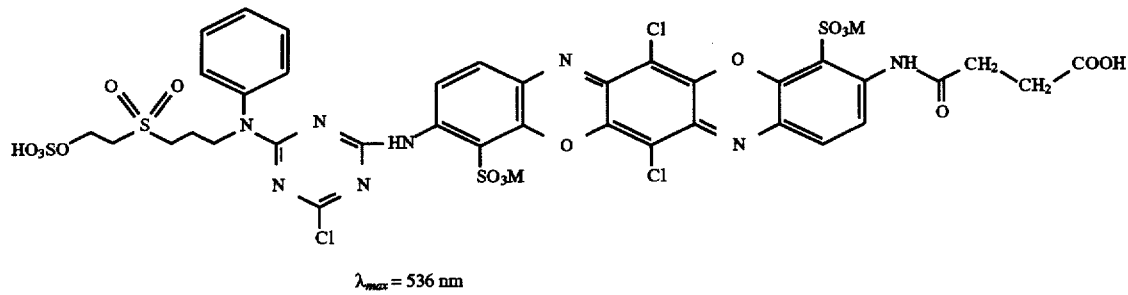

$\lambda_{max} = 536$ nm is obtained. The dyestuff is isolated from the aqueous synthesis solution by salting out with sodium chloride.

The dyestuff dyes cotton in brilliant violet color shades with good fastnesses. The dyestuff is outstandingly suitable for exhaustion dyeings, in which the salt content in the dye liquor corresponds to 10 to 30 g/l.

Example 49

0.14 mol of the compound 2,4-difluoro-6-{N-phenyl-2'-β-sulfato-ethylsulfonyl-ethyl}-amino-triazine is added to 0.1 mol of the freshly prepared compound from Example H in 2 l of water at a pH of 5 to 6 and at a temperature of 20° to 25° C. The mixture is subsequently stirred under a nitrogen atmosphere until the reaction is complete. Stirring is then continued in air at 20° to 250° C. for some time, until the re-oxidation is complete.

The compound of the formula

Example F in 2.5 l of water at a pH of 6 and a temperature of 25° C. The mixture is then heated to 40° C. and subsequently stirred at this temperature under a nitrogen atmosphere, while maintaining a pH of 6, until the reaction is complete. Stirring is then continued in air at 20° to 25° C. for some time, until the re-oxidation is complete. The compound of the formula

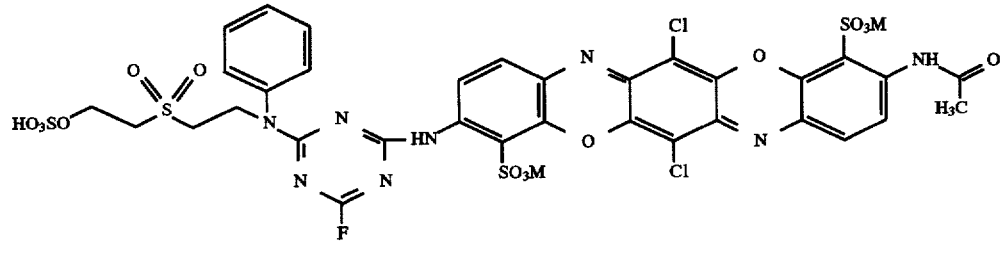

$\lambda_{max} = 535$ nm is obtained. The dyestuff is isolated from the aqueous synthesis solution by salting out with sodium chloride.

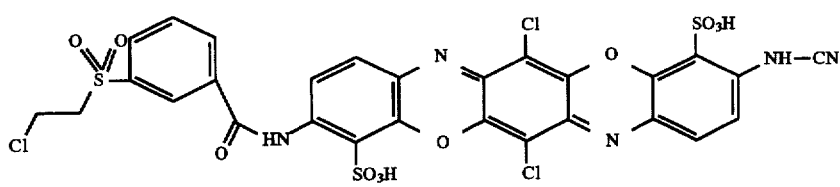

$\lambda = 535$ nm

The dyestuff dyes cotton in brilliant violet color shades with good fastnesses. The dyestuff is outstandingly suitable for exhaustion dyeings, in which the salt content in the dye liquor corresponds to 10 to 20 g/l.

Example 50

0.13 mol of the compound 3-(β-chloroethylsulfonyl)-benzoyl chloride is added to 0.1 mol of the compound from is obtained. The dyestuff is isolated from the aqueous synthesis solution by salting out with sodium chloride.

The dyestuff dyes cotton in brilliant violet color shades with good fastnesses. The dyestuff is outstandingly suitable for exhaustion dyeings, in which the salt content in the dye liquor corresponds to 10 to 30 g/l.

Further examples are shown in Table 5 which are carried out analogously.

TABLE 5

[Structural formula showing: R-C(=O)-NH-phenyl(SO₃H)-N=... chlorinated quinone bridge ...-O-phenyl(SO₃H)-NH-C(=N-A₂)(N=A₁) with Cl substituents and SO₃H groups]

| Ex. No. | R | A₁ | A₂ | Color shade on cotton |
|---|---|---|---|---|
| 51 | β-Carboxy-ethyl | Chloro | N-Phenyl-2-(β-sulfatoethylsulfonyl)-ethyl-amino | violet |
| 52 | β-Carboxy-vinyl | Chloro | N-Phenyl-2-(β-sulfatoethylsulfonyl)-ethyl-amino | violet |
| 53 | 2-Carboxy-phenyl | Chloro | N-Phenyl-2-(β-sulfatoethylsulfonyl)-ethyl-amino | violet |
| 54 | Phenyl | Cyanoamino | N-Phenyl-2-(β-sulfatoethylsulfonyl)-ethyl-amino | violet |
| 55 | 2-Carboxy-phenyl | Chloro | N-Phenyl-2-(β-sulfatoethylsulfonyl)-ethyl-amino | violet |
| 56 | Methyl | Chloro | N-Phenyl-3-(β-sulfatoethylsulfonyl)-propyl-amino | violet |
| 57 | Methyl | Chloro | N-(3-Sulfo-phenyl)-3-(β-sulfato-ethyl-sulfonyl)-propyl-amino | violet |
| 58 | Ethyl | Chloro | N-Phenyl-3-(β-sulfatoethylsulfonyl)-propyl-amino | violet |
| 59 | Ethyl | Fluoro | N-Phenyl-3-(β-sulfatoethylsulfonyl)-propyl-amino | violet |
| 60 | Ethyl | Fluoro | N-Methyl-β-sulfoethyl-amino | violet |
| 61 | Methyl | Fluoro | N-Methyl-2-(β-sulfatoethyl-sulfonyl)-ethylamino | violet |
| 62 | Ethyl | Fluoro | N-Methyl-2-(β-sulfatoethyl-sulfonyl)-ethylamino | violet |
| 63 | β-Carboxy-ethyl | Fluoro | N-Methyl-2-(β-sulfatoethyl-sulfonyl)-ethylamino | violet |
| 64 | β-Carboxy-vinyl | Fluoro | N-Methyl-2-(β-sulfatoethyl-sulfonyl)-ethylamino | violet |
| 65 | 3-(β-Chloro ethyl-sulfonyl)-phenyl | Chloro | β-Sulfoethyl-amino | violet |
| 66 | 3-(β-Chloro ethyl-sulfonyl)-phenyl | Fluoro | β-Sulfoethyl-amino | violet |
| 67 | 3-(β-Chloro ethyl-sulfonyl)-phenyl | Chloro | N-Methyl-β-sulfoethyl-amino | violet |
| 68 | 3-(β-Chloro ethyl-sulfonyl)-phenyl | Chloro | 2,5-Disulfo-phenyl-amino | violet |
| 69 | 3-(β-Chloro ethyl-sulfonyl)-phenyl | Chloro | 4-Sulfo-phenyl-amino | violet |
| 70 | 3-(β-Chloro ethyl-sulfonyl)-phenyl | Cyanoamino | Morpholino | violet |
| 71 | 3-(β-Chloro ethyl-sulfonyl)-phenyl | Cyanoamino | Cyanoamino | violet |
| 72 | 3-(β-Chloro ethyl-sulfonyl)-phenyl | Chloro | 4-(β-Sulfatoethyl)sulfonyl-phenyl-amino | violet |
| 73 | 3-(β-Chloro ethyl-sulfonyl)-phenyl | Chloro | Amino | violet |
| 74 | 3-(β-Chloro ethyl-sulfonyl)-phenyl | β-Sulfoethyl-amino | β-Sulfoethyl-amino | violet |
| 75 | 3-(β-Chloro ethyl-sulfonyl)-phenyl | N-Methyl-β-sulfoethyl amino | N-Methyl-β-sulfoethyl-amino | violet |

Example 76

0.12 mol of the compound 3-(β-chloroethylsulfonyl)-benzoyl chloride is added to 0.1 mol of the freshly prepared leuco compound from Example H in 4 l of water at a pH of 5 and a temperature of 25° C. The mixture is heated to 40° C. and subsequently stirred at this temperature under a nitrogen atmosphere, while maintaining the pH, until the reaction is complete. Stirring is then continued in air at 20° to 25° C., with the addition of 0.1 mol of potassium peroxodisulfate, for some time, until the re-oxidation is complete. The compound of the formula

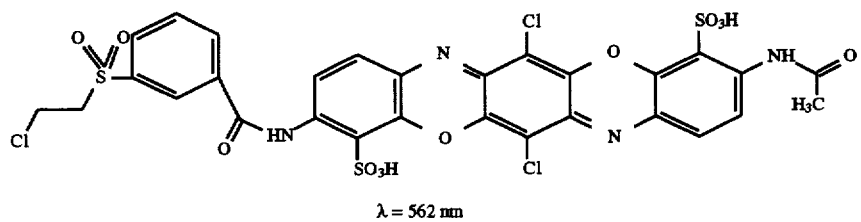

λ = 562 nm is obtained. The dyestuff dyes cotton in brilliant magenta-colored color shades with good fastnesses. The dyestuff is outstandingly suitable for exhaustion dyeings, in which the salt content in the dye liquor corresponds to 10 to 20 g/l.

Example 77

0.12 mol of succinic anhydride is added to 0.1 mol of the leuco compound from Example M in 2 l of water at a pH of 7 and at a temperature of 20° to 25° C. under a nitrogen atmosphere, and the mixture is subsequently stirred at 35° to 40° C. for some time, while maintaining the pH, until the condensation has ended. The nitro group is then reduced in the customary manner with $H_2$ (1 bar) over a Pd-on-charcoal catalyst. The mixture is then subsequently stirred in air for some time, until the re-oxidation to the triphendioxazine compound is complete. The compound of the formula

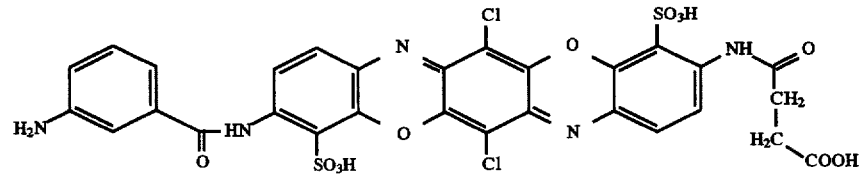

which is isolated by salting out with sodium chloride, is obtained. The resulting product is then dissolved at pH 5 to 6 and at a temperature of 15° to 20° C., and 0.1 mol of 5-chloro-2,4,6-difluoro-pyrimidine is subsequently added. Stirring is then continued in air at 20° to 25° C. for some time, until the reaction is complete. The compound of the formula

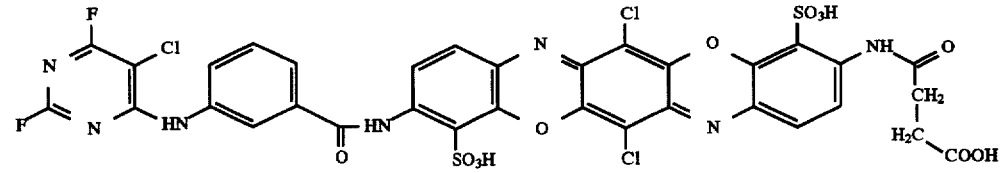

is obtained. The dyestuff dyes cotton in brilliant magenta-colored color shades with good fastnesses. The dyestuff is outstandingly suitable for exhaustion dyeings, in which the salt content in the dye liquor corresponds to 10 to 20 g/l.

The following Table 6 contains further examples according to the formula

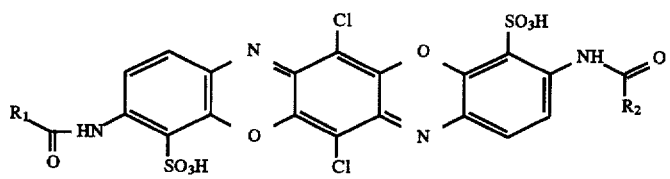

which are prepared in an analogous manner.

TABLE 6

| Ex. No. | R₁ | R₂ | Color shade on cotton |
|---|---|---|---|
| 78 | Ethyl | 3-(β-Chloroethylsulfonyl)-phenyl | magenta |
| 79 | Phenyl | 3-(β-Chloroethylsulfonyl)-phenyl | magenta |
| 80 | 4-Carboxyphenyl | 3-(β-Chloroethylsulfonyl)-phenyl | magenta |

TABLE 6-continued

| Ex. No. | R₁ | R₂ | Color shade on cotton |
|---|---|---|---|
| 81 | 2-Carboxyphenyl | 3-(β-Chloroethylsulfonyl)-phenyl | magenta |
| 82 | 2-Carboxyethyl | 3-(β-Chloroethylsulfonyl)-phenyl | magenta |
| 83 | 2-Carboxyvinyl | 3-(β-Chloroethylsulfonyl)-phenyl | magenta |
| 84 | 3-(β-Chloroethyl-sulfonyl)-phenyl | 3-(β-Chloroethylsulfonyl)-phenyl | magenta |
| 85 | Methyl | 3-(2',4'-Difluoropyrimidin-6'-yl)-amino-phenyl | magenta |
| 86 | Ethyl | 3-(2',4'-Difluoropyrimidin-6'-yl)-amino-phenyl | magenta |
| 87 | Phenyl | 3-(5'-Chloro-2',4'-difluoro-pyrimidin-6'-yl)-amino-phenyl | magenta |
| 88 | 4-Carboxyphenyl | 3-(5'-Cyano-2',4'-dichloro-pyrimidin-6'-yl)-amino-phenyl | magenta |
| 89 | 2-Carboxyphenyl | 3-(2',4',5'-Trichloro-pyrimidin-6'-yl)-amino-phenyl | magenta |
| 90 | 2-Carboxyethyl | 4-(2',4'-Difluoropyrimidin-6'-yl)-amino-phenyl | magenta |
| 91 | 2-Carboxyvinyl | 4-(2',4'-Difluoropyrimidin-6'-yl)-amino-phenyl | magenta |
| 92 | Methyl | 3-(2'-β-Sulfoethyl-4'-fluoro-triazin-6'-yl)-amino-phenyl | magenta |
| 93 | Ethyl | 3-(2'-amino-4'-chloro-triazin-6'-yl)-amino-phenyl | magenta |
| 94 | β-Carboxyethyl | 3-(2'-{2",5"-disulfophenyl}-amino-4'-chloro-triazin-6'-yl)-amino-phenyl | magenta |
| 95 | 2-Carboxy-phenyl | 3-(2'-{4"-sulfophenyl}amino-4'-chloro-triazin-6'-yl)-amino-phenyl | magenta |
| 96 | Methyl | 3-(2'-N-Phenyl-{2"-(β-sulfato-ethyl)-sulfonyl-ethyl}amino-4'-chloro-triazin-6'-yl)-amino-phenyl | magenta |
| 97 | Methyl | 3-(2'-N-Phenyl-{3"-(β-sulfato-ethyl)-sulfonyl-propyl}amino-4'-chloro-triazin-6'-yl)-amino-phenyl | magenta |

Example 98

0.14 mol of 5-chloro-2,4,6-trifluoro-pyrimidine is added to 0.1 mol of the compound from Example Q in 2 l of water at a pH of 5 to 6 and a temperature of 10° to 20° C. The mixture is then heated to 40° C. and subsequently stirred under a nitrogen atmosphere until the reaction is complete. Stirring is then continued in air at 20° to 25° C. for some time, until the re-oxidation is complete. The compound of the formula

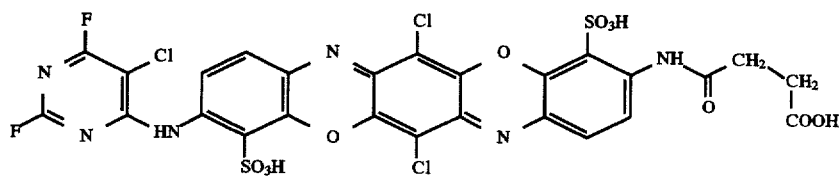

λ = 540 nm is obtained. The dyestuff is isolated from the aqueous synthesis solution by salting out with sodium chloride.

The dyestuff dyes cotton in brilliant violet color shades with good fastnesses. The dyestuff is outstandingly suitable for exhaustion dyeings, in which the salt content in the dye liquor corresponds to 10 to 30 g/l.

Example 99

0.2 mol of 5-chloro-2,4,6-trifluoro-pyrimidine is added to 0.1 mol of the compound from Example F in 3 to 4 l of water at a pH of 5 to 6 and at a temperature of 18° to 22° C. The mixture is subsequently stirred under a nitrogen atmosphere until the reaction is complete. Stirring is then continued in air at 20° to 25° C. for some time, until the re-oxidation is complete.

The compound of the formula

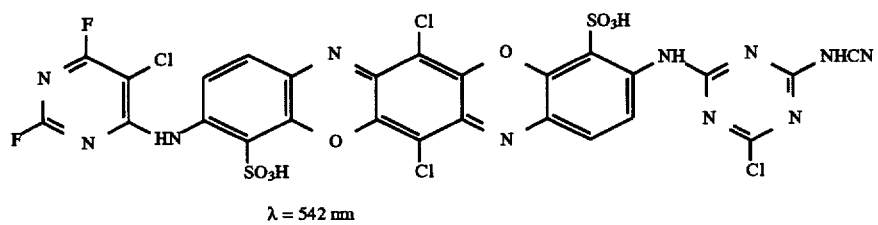

λ = 542 nm is obtained. The dyestuff is isolated from the aqueous synthesis solution by salting out with sodium chloride. The dyestuff dyes cotton in brilliant violet color shades with good fastnesses. The dyestuff is outstandingly suitable for exhaustion dyeings, in which the salt content in the dye liquor corresponds to 10 to 30 g/l.

Table 7 shows further valuable dyestuffs of the formula

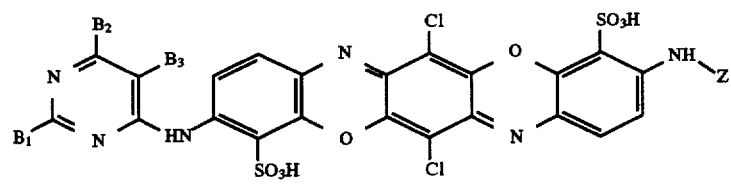

which are prepared in an analogous manner.

TABLE 7

| Ex. No. | $B_1$ | $B_2$ | $B_3$ | Z | Color shade on cotton |
|---|---|---|---|---|---|
| 100 | Fluoro | Fluoro | Hydrogen | Acetyl | magenta |
| 101 | Chloro | Chloro | Cyano | Acetyl | magenta |
| 102 | Chloro | Chloro | Chloro | Propionyl | magenta |
| 103 | Fluoro | Hydrogen | Chloro | Propionyl | magenta |
| 104 | Fluoro | Fluoro | Hydrogen | Propionyl | magenta |
| 105 | Fluoro | Fluoro | Hydrogen | β-Carboxypropionyl | magenta |
| 106 | Fluoro | Fluoro | Hydrogen | β-Carboxypropionyl | magenta |
| 107 | Fluoro | Fluoro | Hydrogen | β-Carboxyacryloyl | magenta |
| 108 | Fluoro | Fluoro | Hydrogen | β-Carboxyacryloyl | magenta |
| 109 | Fluoro | Fluoro | Chloro | 2-Chloro-4-amino-triazin-6-yl | magenta |

TABLE 7-continued

| Ex. No. | $B_1$ | $B_2$ | $B_3$ | Z | Color shade on cotton |
|---|---|---|---|---|---|
| 110 | Fluoro | Fluoro | Chloro | 2-Chloro-4-β-sulfo-ethyl-amino-triazin-6-yl | magenta |
| 111 | Fluoro | Fluoro | Hydrogen | 2-Fluoro-4-{N-methyl-β-sulfo-ethylamino}-triazin-6-yl | magenta |
| 112 | Fluoro | Fluoro | Hydrogen | 2-Chloro-4-cyano-amino-triazin-6-yl | magenta |
| 113 | Fluoro | Hydrogen | Chloro | 5-Chloro-2-fluor-pyrimidin-6-yl | magenta |

Example 114

0.65 mol of 5-chloro-2,4,6-trifluoro-pyrimidine is added to 0.2 mol of the lithium salt of the leuco compound from Example A in 4 l of water at a pH of 6.5 to 7 and at 25° C., lithium hydroxide solution constantly being metered in to maintain the pH at pH 7. The mixture is subsequently stirred until the reaction is complete, and the dyestuff of the formula

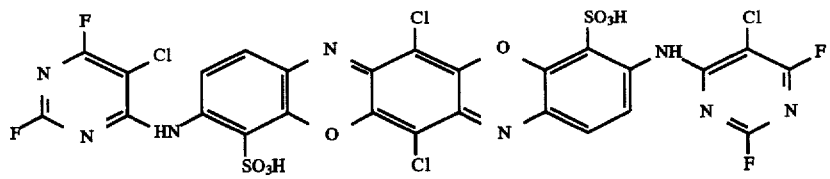

very reddish-tinged blue, $\lambda_{max}$ = 550 nm is isolated by salting out with sodium chloride. The dyestuff dyes cotton in brilliant, very reddish-tinged blue color shades in very high intensities and with good fastnesses, of which the fastnesses to washing are to be emphasized in particular. The fact that the dyestuffs can be used for dyeing with a very small amount of salt, for example with 5 to 10 g/l of sodium sulfate, is particularly advantageous, in particular with respect to ecology.

Example 115

0.5 mol of 2,4,6-trifluoro-pyrimidine is added to 0.2 mol of the lithium salt of the leuco compound from Example A in 3.5 l of water at about 27° C. and a pH of 6.8 to 7.2, lithium hydroxide solution constantly being metered in to maintain the pH at pH 7. The mixture is subsequently stirred until the reaction is complete, and the dyestuff of the formula

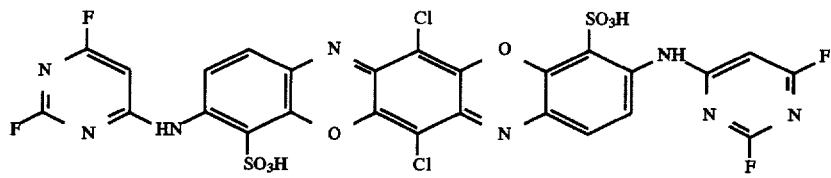

very reddish-tinged blue, $\lambda_{max}=$ 550 nm is isolated by salting out with sodium chloride. The dyestuff dyes cotton in brilliant, very reddish-tinged blue color shades in very high intensities and with good fastnesses, of which the fastnesses to washing are to be emphasized in particular. The fact that the dyestuff can be used for dyeing with a very small amount of salt, for example with 5 to 10 g/l of sodium sulfate, is particularly advantageous, in particular with respect to ecology.

Further reactive dyestuffs are obtained (see the following Table 8), if the procedure is analogous to the preceding examples.

$R_1$ is hydrogen or $C_1$–$C_4$-alkyl, which is optionally substituted by 1 or 2 substituents selected from the group consisting of hydroxyl, $C_1$–$C_4$-alkoxy, sulfato and sulfo;

$R_2$ has one of the meanings of $R_1$;

E is sulfo, carboxyl, $C_1$–$C_4$-alkylsulfonyl or a radical $SO_2Y$, in which Y is vinyl or $CH_2CH_2V$, in which V is hydroxyl, or is a leaving group selected from the group consisting of sulfato, phosphato, thiosulfato and halogen;

or is —$SO_2NR_3R_4$ or —$CONR_3R_4$, in which $R_3$ is hydrogen, phenyl, or $C_1$–$C_4$-alkyl, which is optionally substituted by hydroxyl, carboxyl, sulfo, sulfato or a radical $SO_2Y$, $R_4$ has one of the meanings of $R_3$, or, together with $R_3$ and N, forms a 5- or 6-membered heterocyclic radical, which is optionally interrupted by 1 to 3 further heteroatoms selected from the group consisting of N, O and S;

$X_1$ is halogen, hydrogen, $C_1$–$C_6$-alkyl, phenyl, phenoxy or $C_1$–$C_4$-alkoxy;

$X_2$ has one of the meanings of $X_1$;

TABLE 8

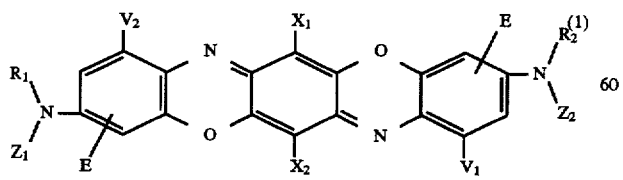

| Ex. No. | $X_1$ | $X_2$ | $X_3$ | Color shade |
|---|---|---|---|---|
| 116 | Chloro | Chloro | Chloro | very reddish-tinged blue |
| 117 | Chloro | Chloro | Cyano | " |
| 118 | Fluoro | Fluoro | Cyano | " |
| 119 | Methylsulfonyl | Methyl | Chloro | " |
| 120 | Hydrogen | Fluoro | Chloro | " |

We claim:

1. A process for the preparation of a triphendioxazine compound of the formula (1)

$V_1$ is hydrogen, sulfo, methoxy, methyl or halogen;

$V_2$ has one of the meanings of $V_1$; and $Z_1$ and $Z_2$ are identical or different and are an acyl radical, an unsubstituted, alkylated or arylated aminocarbonyl radical, a sulfonyl radical or a nitrogen-containing heteroaromatic radical, in which which comprises reducing a compound of the formula (2)

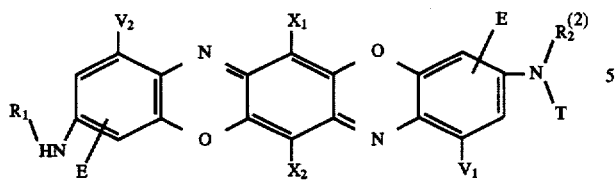

in which T is hydrogen, $Z_1$ or $Z_2$, to give a compound of the formula (3),

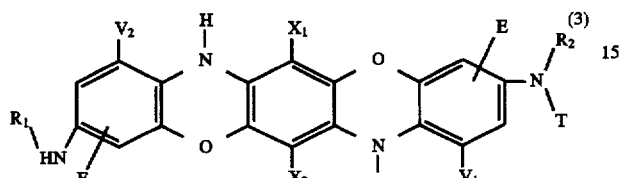

reacting this compound with a reactive derivative on which the radical $Z_1$ or $Z_2$ is based or reacting this compound with reactive derivatives on which the radicals $Z_1$ and $Z_2$ are based, to give a compound of the formula (4)

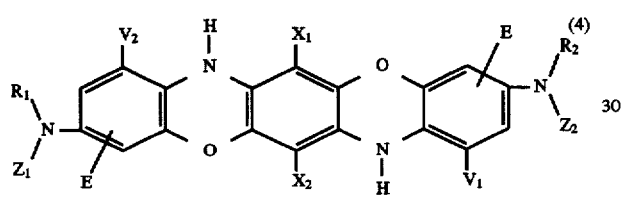

and subsequently oxidizing the compound of the formula (4) to give the triphendioxazine compound of the formula (1).

2. The process as claimed in claim 1, wherein the reduction is carried out in an aqueous medium.

3. The process as claimed in claim 1, wherein the radicals $Z_1$ and $Z_2$ are $C_1$–$C_6$-alkyl-carbonyl, $C_2$–$C_4$-alkenyl-carbonyl, $C_6$-aryl-carbonyl, aminocarbonyl, $C_1$–$C_6$-alkylaminocarbonyl, di-($C_1$–$C_6$)-alkylaminocarbonyl, $C_6$-arylamino-carbonyl or $C_6$-aryl-sulfonyl, in which the alkyl and aryl radicals are optionally substituted by 1 to 3 identical or different substituents selected from the group consisting of $SO_2Y$, sulfo, carboxyl, hydroxyl, $C_1$–$C_4$-alkoxy, $C_1$–$C_4$-alkyl, cyano, halogen, acylamino and nitro; or are radicals of the formulae (5a) to (5d)

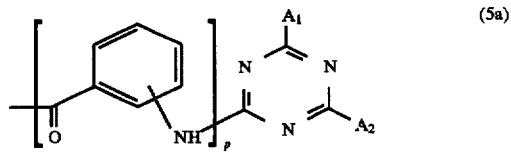

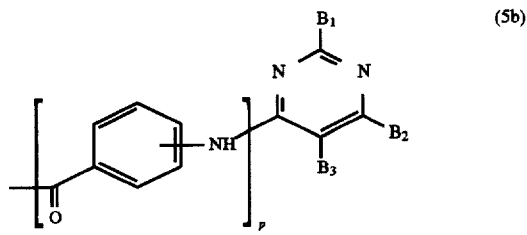

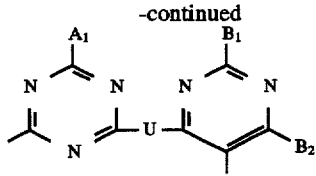

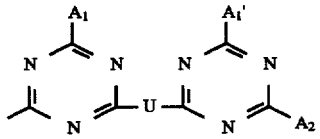

in which p is 0 or 1;

$A_1$ is chlorine, fluorine, $C_1$–$C_4$-alkoxy, phenoxy, hydroxyl, amino, cyanoamino or pyridinyl which is optionally substituted by carboxyl or aminocarbonyl, or a radical $NR_7R_8$, wherein $R_7$ is hydrogen, $C_1$–$C_4$-alkyl, which is optionally substituted by 1 or 2 identical or different substituents selected from the group group consisting of hydroxyl, sulfo, sulfato and carboxyl; or is phenyl, which is optionally substituted by 1 to 3 identical or different substituents selected from the group consisting of methoxy, methyl, halogen, sulfo and carboxyl, $R_8$ is hydrogen or $C_1$–$C_4$-alkyl, which is optionally substituted by 1 to 2 substituents selected from the group consisting of hydroxyl, sulfo, sulfato and carboxyl, or $R_7$ and $R_8$, together with the N atom, form a saturated 5- to 6-membered heterocyclic radical, which optionally contains 1 or 2 others of the hetero atoms N, O, and S or a combination thereof;

$A_2$ has one of the meanings of $A_1$;

$A_1'$ has one of the meanings of $A_1$;

U is a bridge member selected from the group consisting of —NH—$C_1$–$C_6$-alkylene-NH—, —NH—$C_6$-arylene-NH—, in which arylene is optionally substituted by 1 or 2 sulfo, carboxyl, methyl or methoxy radicals or by a combination thereof,

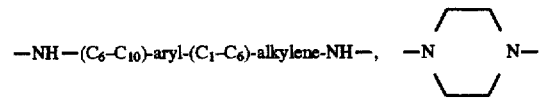

and

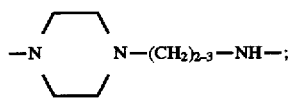

$B_1$ is hydrogen, chlorine, fluorine, trichloromethyl, trifluoromethyl or methylsulfonyl;

$B_2$ is hydrogen, chlorine, methyl, methylsulfonyl or fluorine; and $B_3$ is hydrogen, cyano, fluorine or chlorine, with the proviso that at least one of the radicals $B_1$ or $B_2$ is a leaving group selected from the group consisting of chlorine, fluorine and methylsulfonyl;

or are the radical of the formula (5e)

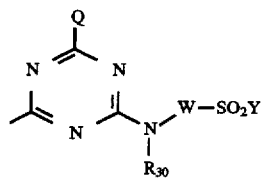

in which

Q is halogen, hydroxyl, cyanoamino or a radical $NR_{30}$—W—$SO_2Y$;

W is $C_2$–$C_6$-alkylene, which is optionally interrupted by a hetero group O, S, NH or $SO_2$, or is phenylene, which is optionally substituted by methoxy or sulfo, or is aralkylene;

$R_{30}$ is hydrogen, $C_1$–$C_4$-alkyl, phenyl, which is optionally substituted by a sulfo group, or is the radical —$W_1$—$SO_2Y$, in which $W_1$ is $C_2$–$C_6$-alkyl, and Y has one of the meanings given in claim 1.

4. The process as claimed in claim 1, wherein $Z_1$ and $Z_2$ are identical or different and are radicals of the formulae

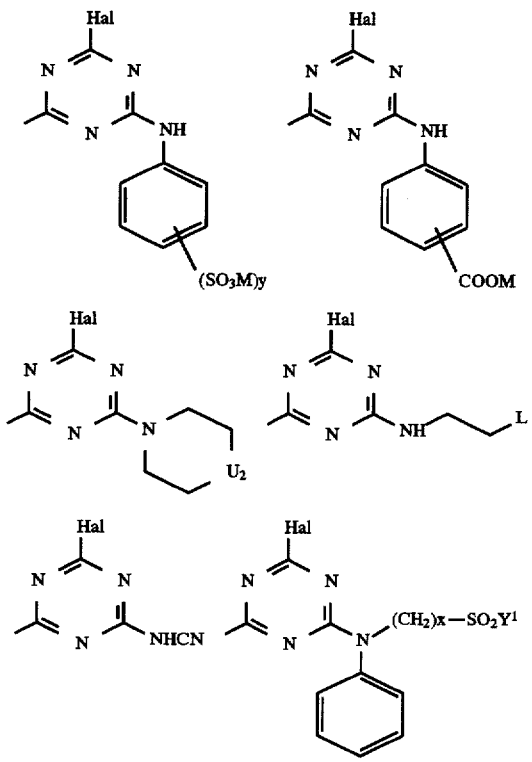

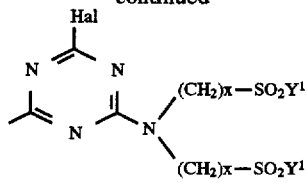

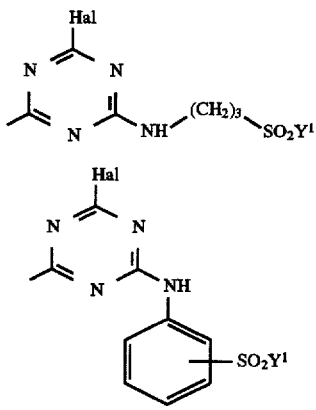

in which

X is 2 or 3;

Y is 1 or 2;

$U_2$ is a chemical bond, methylene, —O—, —NH—, >N($CH_2$)$_2$OH, —S— or —$SO_2$—;

L is hydroxyl, sulfo, carboxyl or sulfato;

$Y^1$ is vinyl, β-sulfatoethyl, β-chloroethyl or β-hydroxyethyl;

Hal is chlorine or fluorine, and

M is hydrogen or an alkali metal.

5. The process as claimed in claim 1, where $Z_1$ and $Z_2$ are identical, wherein the compound of the formula (3) in which T has the meaning of hydrogen is reacted with 2 to 6 times the molar amount of the reactive derivative on which the radical $Z_1$ or $Z_2$ is based.

6. The process as claimed in claim 1, wherein $Z_1$ and $Z_2$ are different, wherein the compound of the formula (3) in which T has the meaning of $Z_1$ is reacted with 1 to 3 times the molar amount of the reactive derivative on which the radical $Z_2$ is based.

7. The process as claimed in claim 1, wherein the reactive derivative on which the radicals $Z_1$ and $Z_2$ are based is an organic or inorganic acid halide or anhydride, an isocyanate, a carbonic acid ester, urea, a carbamic acid chloride, a halotriazine or a halopyrimidine.

* * * * *